US008314083B2

(12) United States Patent
Du

(10) Patent No.: US 8,314,083 B2
(45) Date of Patent: *Nov. 20, 2012

(54) NON-SEDATING ANTIHISTAMINE INJECTION FORMULATIONS AND METHODS OF USE THEREOF

(75) Inventor: Jie Du, Lansdale, PA (US)

(73) Assignee: JDP Therapeutics, Inc., Lansdale, PA (US)

( * ) Notice: Subject to any disclaimer, the term of this patent is extended or adjusted under 35 U.S.C. 154(b) by 64 days.

This patent is subject to a terminal disclaimer.

(21) Appl. No.: 12/829,857

(22) Filed: Jul. 2, 2010

(65) Prior Publication Data
US 2011/0004164 A1 Jan. 6, 2011

Related U.S. Application Data

(63) Continuation-in-part of application No. 12/704,089, filed on Feb. 11, 2010, now Pat. No. 8,263,581.

(60) Provisional application No. 61/248,441, filed on Oct. 3, 2009, provisional application No. 61/222,951, filed on Jul. 3, 2009.

(51) Int. Cl.
*A61K 31/56* (2006.01)
(52) U.S. Cl. ........................................ 514/171
(58) Field of Classification Search .................. None
See application file for complete search history.

(56) References Cited

U.S. PATENT DOCUMENTS

| 4,117,141 | A | 9/1978 | Michaeli |
| 4,434,237 | A | 2/1984 | Dinarello |
| 4,525,358 | A | 6/1985 | Baltes et al. |
| 4,826,689 | A | 5/1989 | Violanto et al. |
| 5,276,044 | A | 1/1994 | Ambrus et al. |
| 5,419,898 | A | 5/1995 | Ikejiri et al. |
| 5,492,935 | A | 2/1996 | Yu et al. |
| 5,627,183 | A | * | 5/1997 | Gray ........................ 514/255.04 |
| 5,698,558 | A | 12/1997 | Gray |
| 6,258,816 | B1 | 7/2001 | Singh et al. |
| 6,319,927 | B1 | 11/2001 | Martin |
| 6,384,038 | B1 | 5/2002 | Rubin |
| 6,432,961 | B1 | 8/2002 | Uylenbroeck et al. |
| 6,451,815 | B1 | 9/2002 | Hwange et al. |
| 6,509,014 | B1 | 1/2003 | De Lacharriere et al. |
| 6,537,573 | B2 | 3/2003 | Johnson et al. |
| 6,660,301 | B1 | 12/2003 | Vogel et al. |
| 6,670,384 | B2 | 12/2003 | Bandypadhyay et al. |
| 6,720,001 | B2 | 4/2004 | Chen et al. |
| 6,790,847 | B2 | 9/2004 | Walch |
| 6,824,786 | B2 | 11/2004 | Yu et al. |
| 7,026,360 | B1 | 4/2006 | Festo |
| 7,115,563 | B2 | 10/2006 | Younis et al. |
| 7,338,657 | B2 | 3/2008 | Vogel et al. |
| 2001/0038863 | A1 | 11/2001 | Jaenicke et al. |
| 2002/0012700 | A1 | 1/2002 | Johnson et al. |
| 2002/0031558 | A1 | 3/2002 | Yoo |
| 2002/0048596 | A1 | 4/2002 | Cevc |
| 2002/0164374 | A1 | 11/2002 | Jackson et al. |
| 2002/0169190 | A1 | 11/2002 | Bandyopadhyay et al. |
| 2003/0068375 | A1 | 4/2003 | Wright et al. |
| 2003/0108496 | A1 | 6/2003 | Yu et al. |
| 2003/0134810 | A1 | 7/2003 | Springate et al. |
| 2003/0134811 | A1 | 7/2003 | Jackson et al. |
| 2003/0143184 | A1 | 7/2003 | Seo et al. |
| 2003/0144336 | A1 | 7/2003 | Chen et al. |
| 2003/0211083 | A1 | 11/2003 | Vogel et al. |
| 2004/0077540 | A1 | 4/2004 | Quay |
| 2004/0142852 | A1 | 7/2004 | Younis et al. |
| 2004/0185145 | A1 | 9/2004 | Ehrman et al. |
| 2004/0197324 | A1 | 10/2004 | Liu et al. |
| 2004/0203145 | A1 | 10/2004 | Zamore et al. |
| 2004/0228831 | A1 | 11/2004 | Belinka, Jr. et al. |
| 2004/0247660 | A1 | 12/2004 | Singh |
| 2004/0268425 | A1 | 12/2004 | Bookbinder et al. |
| 2005/0031667 | A1 | 2/2005 | Patel et al. |
| 2005/0031713 | A1 | 2/2005 | Ehrich et al. |
| 2005/0032173 | A1 | 2/2005 | Rojas et al. |
| 2005/0042293 | A1 | 2/2005 | Jackson et al. |
| 2005/0147607 | A1 * | 7/2005 | Reed ........................ 424/145.1 |
| 2005/0158408 | A1 | 7/2005 | Yoo |
| 2005/0202090 | A1 | 9/2005 | Clarke |
| 2005/0208134 | A1 | 9/2005 | Magdassi et al. |
| 2005/0260186 | A1 | 11/2005 | Bookbinder et al. |
| 2005/0282879 | A1 | 12/2005 | Salehani |
| 2006/0002963 | A1 | 1/2006 | Rabinovich-Guilatt et al. |
| 2006/0079558 | A1 | 4/2006 | Aberg et al. |
| 2006/0079559 | A1 | 4/2006 | Aberg et al. |
| 2006/0079846 | A1 | 4/2006 | Williams |
| 2006/0084683 | A1 | 4/2006 | Uylenbroeck et al. |

(Continued)

FOREIGN PATENT DOCUMENTS

EP    1005865 A1    6/2000

(Continued)

OTHER PUBLICATIONS

Banerji et al (Allergy Astham Proc 28:418-426, 2007).*
Metoclopramide Injection, Solution (archived drug label, Jun. 2006; available online at http://dailymed.nlm.nih.gov).*
Allegra (fexofenadine hydrochloride) tablets; product label; Allegra ODT manufactured for sanofi-aventis U.S. LLC; 19 pages, 2007.
Banerji et al. "Diphenhydramine versus nonsedating antihistamines for acute allergic reactions: A literature review" Jul.-Aug. 2007, *Allergy and Asthma Proceedings* 28(4):418-426.
Coyle et al. "The effect of cetirizine on antigen-dependent leucopenia in the guinea-pig" Jun. 1991, *Br. J. Pharmacol.* 103(2):1520-1524.
Desager et al. "A pharmacokinetic evaluation of the second-generation H1-receptor antagonist cetirizine in very young children" Apr. 1993, *Clin. Pharmacol. Ther.* 53(4):431-435.
Dux et al. "Possible role of histamine (H1- and H2-) receptors in the regulation of meningeal blood flow" Nov. 2002, *Br. J. Pharmacol.* 137(6):874-880.

(Continued)

*Primary Examiner* — Craig Ricci
(74) *Attorney, Agent, or Firm* — Cantor Colburn LLP

(57) ABSTRACT

Disclosed are injectable formulations of cetirizine for treating acute allergic reactions and methods for treating acute allergic reactions. In particular, an intravenous injectable is disclosed as are methods of treating acute allergic reactions therewith.

12 Claims, No Drawings

U.S. PATENT DOCUMENTS

| | | |
|---|---|---|
| 2006/0095075 A1 | 5/2006 | Burkinshaw et al. |
| 2006/0104968 A1 | 5/2006 | Bookbinder et al. |
| 2006/0106364 A1 | 5/2006 | Whitlock et al. |
| 2006/0148903 A1 | 7/2006 | Burch et al. |
| 2006/0210604 A1 | 9/2006 | Dadey et al. |
| 2006/0211754 A1 | 9/2006 | Yu et al. |
| 2006/0216363 A1 | 9/2006 | Liu et al. |
| 2006/0241017 A1 | 10/2006 | Chandran |
| 2006/0247258 A1 | 11/2006 | Revirron |
| 2006/0287244 A1 | 12/2006 | Chandran |
| 2007/0014843 A1 | 1/2007 | Dobak |
| 2007/0020196 A1 | 1/2007 | Pipkin et al. |
| 2007/0021326 A1 | 1/2007 | Hamid et al. |
| 2007/0026058 A1 | 2/2007 | Pereswetoff-Morath et al. |
| 2007/0053900 A1 | 3/2007 | Liu et al. |
| 2007/0128276 A1 | 6/2007 | Jain et al. |
| 2007/0166368 A1 | 7/2007 | Singh |
| 2007/0191781 A1 | 8/2007 | Richards et al. |
| 2007/0203247 A1 | 8/2007 | Phillips et al. |
| 2007/0213660 A1 | 9/2007 | Richards et al. |
| 2007/0219498 A1 | 9/2007 | Malone et al. |
| 2007/0264349 A1 | 11/2007 | Lee et al. |
| 2007/0281947 A1 | 12/2007 | Matsumori |
| 2007/0286881 A1 | 12/2007 | Burkinshsw |
| 2008/0027030 A1 | 1/2008 | Stogniew et al. |
| 2008/0064721 A1 | 3/2008 | Rohrs et al. |
| 2008/0066741 A1 | 3/2008 | LeMahieu et al. |
| 2008/0103564 A1 | 5/2008 | Burkinshaw et al. |
| 2008/0145405 A1 | 6/2008 | Kunzler et al. |
| 2008/0145419 A1 | 6/2008 | Gibson et al. |
| 2008/0152708 A1 | 6/2008 | Gibson et al. |
| 2008/0214649 A1 | 9/2008 | Yu et al. |
| 2008/0294261 A1 | 11/2008 | Pauza et al. |
| 2008/0311171 A1 | 12/2008 | Patel et al. |
| 2009/0010924 A1 | 1/2009 | Wu et al. |
| 2009/0048268 A1 | 2/2009 | Asotra et al. |
| 2009/0054994 A1 | 2/2009 | Rogan et al. |
| 2009/0123367 A1 | 5/2009 | Bookbinder et al. |
| 2009/0137606 A1 | 5/2009 | Cohen |
| 2009/0156504 A1 | 6/2009 | Siegel et al. |
| 2009/0181908 A1 | 7/2009 | Kaspar et al. |
| 2009/0186038 A1 | 7/2009 | Reed |
| 2009/0216183 A1 | 8/2009 | Minotti |
| 2009/0227564 A1 | 9/2009 | Sugamata |
| 2009/0280129 A1 | 11/2009 | Liu et al. |
| 2009/0298869 A1 | 12/2009 | Burnier et al. |
| 2009/0304648 A1 | 12/2009 | Owen |
| 2009/0311311 A1 | 12/2009 | Shantha et al. |
| 2009/0312706 A1 | 12/2009 | Shantha et al. |
| 2010/0008996 A1 | 1/2010 | Meinert |
| 2010/0022496 A1 | 1/2010 | Perovitch et al. |
| 2010/0029662 A1 | 2/2010 | Horn |
| 2010/0069402 A1 | 3/2010 | Melamed |
| 2011/0008325 A1 | 1/2011 | Pipkin et al. |
| 2012/0053563 A1 | 3/2012 | Du |

FOREIGN PATENT DOCUMENTS

| | | |
|---|---|---|
| EP | 1109557 B1 | 11/2002 |
| EP | 1098870 B1 | 10/2005 |
| WO | WO 98/00159 A1 | 1/1998 |
| WO | WO 98/22130 A1 | 5/1998 |
| WO | WO 00/06531 A2 | 2/2000 |
| WO | WO 01/28555 A1 | 4/2001 |
| WO | WO 02/47689 A2 | 6/2002 |
| WO | WO 2004/084865 A1 | 10/2004 |
| WO | WO 2009/044141 A1 | 4/2009 |

OTHER PUBLICATIONS

Epipen (epinephrine) Auto-Injector 0.3 mg; label; *Meridian Medical Technologies, Inc., Manufactured for Dey L.P.*, 7 pages, Sep. 2008.
International Search Report and Written Opinion dated Aug. 30, 2010 for PCT/US2010/040925.
Jaber et al. "Determination of cetirizine dihydrochloride, related impurities and preservatives in oral solution and tablet dosage forms using HPLC" Oct. 29, 2004, *J. Pharm. Biomed. Anal.* 36(2):341-350.
Krause "Anaphylaxis" updated Sep. 2, 2009, eMedicine.com.
Lieberman "The use of antihistamines in the prevention and treatment of anaphylaxis and anaphylactoid reactions" Oct. 1990, *J. Allergy Clin. Immunol.* 86(4/2):684-686.
Linzer Sr. "Pediatrics, Anaphylaxis" updated Mar. 29, 2011, eMedicine.com, 9 pages (TOC).
Salzberg et al. "Anaphylaxis: When Seconds Count" 2007, *Emerg. Med.* 39(5):18-24.
Sampson "Anaphylaxis and Emergency Treatment" 2004, *Pediatrics* 111(6):1601-1608.
Sampson et al. "Symposium on the Definition and Management of Anaphylaxis: Summary Report" 2005, *J. Allergy Clin. Immunol.* 115(3):584-591.
Xyzal (levocetirizine dihydrochloride) 5 mg. tablets; product label; *UCB, Inc.*; 9 pages, 2009.
Zyrtec-D 12 Hour (Cetirizine Hydrochloride 5 mg and Pseudoephedrine Hydrochloride 120 mg) Extended Release Tablets; product label; *Pfizer labs; Marketed by UCB Pharma, Inc.*, 12 pages; revised Aug. 2003.
U.S. Appl. No. 12/704,089, filed Feb. 11, 2010, NonFinal Office Action of Aug. 5, 2011, 19 pages.
Tillement et al., "Compared pharmacological characteristics in humans of racemic cetirizine and levocetirizine, two histamine H1-receptor antagonists," Biochemical Pharmacology vol. 66, No. 7, Oct. 1, 2003, pp. 1123-1126.
Pfizer Labs, "Zyrtec", May 1, 2006, online drug review, retrieved Aug. 17, 2010, from pfizer.com/files/products/uspi_zyrtec.pdf.
U.S. Appl. No. 13/291,514, filed Nov. 8, 2011 NonFinal Office Action Mailed Aug. 31, 2012, 29 pages.
U.S. Appl. No. 12/704,089, filed Feb. 11, 2010, Jie Du, NonFinal Office Action 12.
Annals of Allergy, Asthma & Immunology; 85; pp. 525-531; (2000).
Hydroxyzine Description; American Regent Labortories, Inc.; 9 pages; Revised: Nov. 2006.
Linder et al.; ""Hydroxyzine Hemolysis in Surgical Patients"; Anesthesia and Analgesia"; 46(1); 6 pages; (1967).
"Hydroxyzine"; 2006 Lippincott's Nursing Drug Guide; ed. Lippincott Williams & Wilkins; http://web.sqe.edu.om/med-Lib/MED_CD/E_CDs/Nursing%20Drug%20Guide/mg/hydroxyzine.htm; (2006).
"Hydroxyzine (Atarax) Adverse Reactions"; RX-s.net Online pharmacy; http://rx-s.net/weblog/more/atarax_adverse_reactions/; last revised: Dec. 11, 2002.
Shands "Drugs & Therapy Bulletin"; 15(6) 4 pages; (2001).
Tokodi, Jr., et al.; "Massive Tissue Necrosis After Hydroxyzine Injection"; J. Am Osteopath Assoc; 95(10); p. 609; Abstract only; (1995).
Winbery, et al.; "Histamine and Antihistamines in Anaphylasix"; Clin Allergy Immunol; 17; pp. 287-317; Abstract only (2002).
"Hydroxyzine"; 2006 Lippincott's Nursing Drug Guide; ed. Lippincott Williams & Wilkins; http://web.sqe.edu.om/med-Lib/MED_CD/E_CDs/Nursing%20Drug%20Guide/mg/hydroxyzine.htm; (2006).

* cited by examiner

NON-SEDATING ANTIHISTAMINE INJECTION FORMULATIONS AND METHODS OF USE THEREOF

CROSS REFERENCE TO RELATED APPLICATION

This application is a nonprovisional of U.S. Provisional Application Ser. Nos. 61/248,441 filed Oct. 3, 2009, 61/222,951 filed Jul. 3, 2009, and updated Jul. 6, 2009, and a continuation-in-part of U.S. patent application Ser. No. 12/704,089 filed on Feb. 11, 2010, all which are hereby incorporated by reference in their entirety.

BACKGROUND

Acute allergic reaction, ranging from the mild cases of urticaria to the most severe cases of anaphylaxis, is a systemic, immediate hypersensitivity reaction caused by exposure to a specific antigen. The immune system activates immunoglobulin E (IgE), which reacts with effector cells (mast cells and basophils). These cells, in turn, release histamine, serotonin, leukotrienes, and prostaglandins, and induce a range of signs and symptoms, such as facial flushing, urticaria (hives), angioedema, pruritus, erythema, wheezing, bronchoconstriction, cough, cardiac arrhythmias, hypotension, nausea, vomiting, and diarrhea. Cutaneous manifestations are most common, with urticaria and/or angioedema present in 88% or more of patients experiencing acute allergic reactions. Swelling in the airway is the most life threatening symptom, commonly causing dyspnea, wheezing, stridor, and upper airway obstruction from severe edema. Cardiovascular symptoms include dizziness, hypotension, and syncope related to third-spacing of intravascular fluid. Common gastrointestinal manifestations include nausea, vomiting, abdominal pains or cramps, and diarrhea. Although symptoms vary between acute allergy patients, onset generally occurs seconds to minutes after exposure to an allergen and requires prompt treatment.

The true incidence of acute allergic reactions is unknown, partly because of the lack of a precise definition of the syndrome. Some clinicians reserve the term anaphylaxis for the full-blown syndrome, while others use it to describe milder cases. Fatal anaphylaxis is relatively rare; milder forms occur much more frequently. The frequency of acute allergic reaction is increasing, and this has been attributed to the increased number of potential allergens to which people are exposed, such as increased varieties of food and medications. A recent review concluded that the lifetime prevalence of acute allergic reactions is ~5% of the population with higher prevalence in developed countries than developing countries.

Approximately 1 in 5000 exposures to a parenteral dose of penicillin or cephalosporin antibiotic causes anaphylaxis. More than 100 deaths per year are reported in the United States due to antibiotic induced allergies. Fewer than 100 fatal reactions to Hymenoptera stings are reported each year in the United States, but this is considered to be an underestimate. One to 2% of people receiving IV radiocontrast experience some sort of reaction. The majority of these reactions are minor, and fatalities are rare. Low molecular weight contrast causes fewer and less severe reactions. Narcotics also induce acute allergic reactions.

Acute allergic reactions occur in all age groups. Food allergies are more common in the young, whereas more drug reactions occur in adults, possibly due to greater exposure to medications, including narcotics, aspirin/NSAIDs, antibiotics, IV contrast media, anesthesia, chemo agents, muscle relaxants, etc. Although prior exposure is essential for the development of true anaphylaxis, reactions occur even when no documented prior exposure exists. Thus, patients may react to a first exposure to an antibiotic or insect sting. Elderly persons have the greatest risk of mortality from acute allergic reactions due to the presence of preexisting disease.

Emergency treatment includes airway protection, alpha-agonists, antihistamines, steroids, and beta agonists. Medications currently used in the treatment of acute allergic reactions include epinephrine, diphenhydramine injection, corticosteroids, albuterol, and glucagon. Epinephrine is the first-line drug to be given to a patient having an acute allergic reaction including anaphylaxis. Where breathing issues or airway constriction is an issue, epinephrine should remain the first-line drug. The first generation antihistamines (intramuscular hydroxyzine and injectable diphenhydramine) are used as the second-line drug to be given to a patient having an acute allergic reaction as an adjunct therapy to epinephrine for the relief of peripheral symptoms such as pruritus, engioedema, urticaria (hives), erythema, wheezing, etc. An alpha-receptor agonist, epinephrine reverses hypotension. It also has beta-receptor activity, which dilates the airways, increases the force of myocardial contraction, and suppresses histamine and leukotriene release, reducing inflammatory responses. Where airway constriction or breathing issues are being controlled or are not concerned, first generation antihistamines such as oral, intramuscular hydroxyzine, or injectable diphenhydramine injection may be used alone without epineprhine.

In cases where airway constriction or other breathing and respiratory issues are not a concern, or where they are being controlled, better treatments are still needed. The current treatment with first generation antihistamines suffers from several drawbacks, including their short half-lives, their highly sedative nature, the large number of potential drug/drug interactions, the potential cardiotoxicity (QT prolongation), and other potential side effects. Accordingly, new treatments for acute allergic reactions are needed, particularly for use in the emergency setting.

SUMMARY

Some embodiments of the invention provide an injectable formulation for treating acute allergic reaction comprising:
about 0.1% to about 2% w/v of cetirizine, a pharmaceutically acceptable salt, or polymorph, thereof;
about 0.1 to about 0.9% w/v NaCl;
with pH adjusted to about 3 to about 9;
and Q.S. water;
In some embodiments, the injectable is a single dosage form comprising about 0.2 ml to about 10 mL. In further embodiments, the injectable is about 0.5 mL to about 5 mL. In still further embodiments, the injectable is about 1 mL.

In some embodiments, the formulation is substantially free of a buffer.

In some embodiments, the injectable form is a single dose form, suitable for delivering about 10 mg per dose.

In some embodiments, cetirizine is cetirizine HCl and is present at about 1% w/v in a 1 mL injectable single dosage form.

In some embodiments, the injectable is suitable for direct injection without dilution.

In some embodiments, the injectable is suitable for Intravenous injection.

In some embodiments the formulation is for once daily administration.

Some embodiments of the invention provide an injectable formulation for treating acute allergic reaction comprising:
about 1% w/v cetirizine, a pharmaceutically acceptable salt, or polymorph, thereof;
about 0.65% w/v NaCl; and
adjusted to about pH 5.4;
in a 1 mL single dosage form.

Some embodiments provide an injectable formulation for treating acute allergic reaction consisting essentially of:
about 1% w/v cetirizine or a pharmaceutically acceptable salt thereof;
about 0.65% w/v NaCl; and
adjusted to about pH 5.4;
in a 1 mL single dosage form.

Some embodiments provide an injectable formulation for treating acute allergic reaction consisting of:
about 1% w/v cetirizine or a pharmaceutically acceptable salt thereof;
about 0.65% w/v NaCl; and
adjusted to about pH 5.4;
in a 1 mL single dosage form.

In some embodiments, the injectable composition further comprises a second active agent comprising ranitidine, cimetidine, epinephrine, methylprednisolone, prednisolone, thereof. or a combination thereof.

Some embodiments provide an injectable formulation for treating acute allergic reaction comprising:
about 0.05% to about 1% w/v of levocetirizine, a pharmaceutically acceptable salt, or polymorph, thereof;
about 0.1 to about 0.9% w/v NaCl;
with pH adjusted to about 3 to about 9; and Q.S. water.

Some embodiments of the invention provide a method of treating an acute allergic reaction, comprising:
administering to a patient in need thereof an effective amount of injection, as described herein, of cetirizine a pharmaceutically acceptable salt, or polymorph, thereof; and
informing the patient or a medical care worker that injection of cetirizine, or salt, or polymorph, is unlikely to produce, or be subject to metabolic drug/drug interactions.

Some embodiments provide a method of treating an acute allergic reaction while minimizing drug/drug interactions or possible drug overdose or under dose, comprising:
identifying a patient potentially suffering from an acute allergic reaction;
administering, to said identified patient, an amount of injectable cetirizine, a pharmaceutically acceptable salt, or polymorph, thereof, without regard for the recent drug intake history of said identified patient.

In some embodiments, the administration occurs in the absence of the patient recent drug intake history. Such treatments are particularly useful in the emergency room setting.

In some embodiments, the method of treatment is carried out when patient has been or is believed to have been administered a first generation antihistamine prior to said identifying step.

In some embodiments, the administration is performed with or without full knowledge of the patient's recent medication intake history including current use of first generation antihistamine.

In some embodiments, the injection of cetirizine or a pharmaceutically acceptable salt thereof comprises:
about 0.1% to about 2% w/v of cetirizine or a pharmaceutically acceptable salt thereof;
about 0.1 to about 0.9% w/v NaCl;
with pH adjusted to about 3 to about 9; and Q.S. water.

In some embodiments, the injection of cetirizine or a pharmaceutically acceptable salt thereof is an intravenous injection comprising:
about 1% w/v cetirizine or a pharmaceutically acceptable salt thereof;
about 0.65% w/v NaCl; and
adjusted to about pH 5.4;
in a 1 mL single dosage form.

In some embodiments, the acute allergic reaction is selected from urticaria, angiodema, pruritis, erythema, wheezing, or combinations thereof.

Some embodiments provide a method of treating acute allergic reaction in a patient requiring no further sedation, comprising:
injecting, into a patient in need of such treatment, an injectable solution of cetirizine or a pharmaceutically acceptable salt, polymorph thereof.

In some embodiments, the injection of cetirizine or a pharmaceutically acceptable salt thereof comprises:
about 0.1% to about 2% w/v of cetirizine or a pharmaceutically acceptable salt thereof;
about 0.1 to about 0.9% w/v NaCl;
with pH adjusted to about 3 to about 9; and Q.S. water.

In some embodiments, the injection of cetirizine or a pharmaceutically acceptable salt thereof is an intravenous injection, comprising:
about 1% w/v cetirizine or a pharmaceutically acceptable salt thereof;
about 0.65% w/v NaCl; and
adjusted to about pH 5.4;
in a 1 mL single dosage form.

Some embodiments, further comprise monitoring said patient until a reduction of allergic symptoms is achieved.

Some embodiments further comprise stopping said patient monitoring upon indication of sufficient reduction of allergic symptoms. Due to the lack of or reduced sedative effect, additional monitoring is believed to be unnecessary.

In some embodiments, the monitoring does not include additional monitoring sedation.

In some embodiments, the patient is initially sedated or unsedated. In some embodiments, the patient is initially sedated.

Some embodiments provide a method of treating an acute allergic reaction comprising:
administering via an injection composition of a hydroxyzine metabolite or a pharmaceutically acceptable salt, or polymorph, thereof which is substantially free from hemolytic effect to a patient in need of such treatment.

In some embodiments, the hydroxyzine metabolite is cetirizine or a pharmaceutically acceptable salt, or polymorph, thereof.

In some embodiments, the injection comprises:
about 0.1% to about 2% w/v of cetirizine or a pharmaceutically acceptable salt thereof;
about 0.1 to about 0.9% w/v NaCl;
with pH adjusted to about 3 to about 9; and Q.S. water.

In some embodiments, the injection is an intravenous injection comprising:
about 1% w/v cetirizine or a pharmaceutically acceptable salt thereof;
about 0.65% w/v NaCl; and
adjusted to about pH 5.4;
in a 1 mL single dosage form.

Some embodiments provide a method for treating urticaria and/or angioedema comprising:
administering to a patient in need of such treatment of injection composition of cetirizine, or a pharmaceutically acceptable salt, or polymorph, thereof, in an amount of effective to treat said urticaria and/or angioedema while minimizing sedation, free of hemolytic potential, or without demonstrating an effect on the QTc interval.

In some embodiments, the injection comprises:
about 0.1% to about 2% w/v of cetirizine or a pharmaceutically acceptable salt thereof;
about 0.1 to about 0.9% w/v NaCl;
with pH adjusted to about 3 to about 9; and Q.S. water.

In some embodiments, the injection is an intravenous injection comprising:
about 1% w/v cetirizine or a pharmaceutically acceptable salt thereof;
about 0.65% w/v NaCl; and
adjusted to about pH 5.4;
in a 1 mL single dosage form.

Some embodiments provide a method of treating acute allergic reaction in a patient comprising:
identifying a patient in need of such treatment in whom treatment with first-generation antihistamine is undesirable or unsuitable;
injecting, into a patient in need of such treatment, an injectable composition of cetirizine or a pharmaceutically acceptable salt, polymorph thereof.

In some embodiments, the patient for whom first generation antihistamine is undesirable or unsuitable includes ambulatory elderly patients, OB-gyn patients, sedated patients, patients with cardiac risk, patients with multiple attacks of acute allergic reactions within a few hours, patients on multiple drugs, patients with unknown drug profiles, and/or those for whom sedation is undesirable.

In some embodiments, the injectable solution comprises:
about 0.1% to about 2% w/v of cetirizine or a pharmaceutically acceptable salt thereof;
about 0.1 to about 0.9% w/v NaCl
with pH adjusted to about 3 to about 9; and Q.S. water;

In some embodiments, the injectable solution is an intravenous injection comprising:
about 1% w/v cetirizine or a pharmaceutically acceptable salt thereof;
about 0.65% w/v NaCl; and
adjusted to about pH 5.4;
in a 1 mL single dosage form.

In some embodiments, the acute allergic reaction is selected from urticaria, angiodema, pruritis, erythema, wheezing, or combinations Some embodiments provide a method of treating an acute allergic reaction comprising:
administering to a patient in need thereof an injectable formulation comprising about 10 mg cetirizine or a pharmaceutically acceptable salt, polymorph thereof; whose duration of action lasts for about 24 hours, is administered once daily.

Some embodiments provide an automatic injector designed to allow a user to self-administer a pre-measured dose of a composition of injectable non-sedating antihistamine, subcutaneously or intramuscularly, comprising a housing comprising a chamber for the non-sedating antihistamine composition and a dispensing assembly in communication with the chamber, wherein the non-sedating antihistamine composition comprises an injectable solution of cetirizine or a pharmaceutically acceptable salt, or polymorph, thereof.

In some embodiments, the the non-sedating antihistamine composition further comprises ranitidine, cimetidine, epinephrine, methylprednisolone, prednisolone, or a combination thereof.

Some embodiments provide a kit comprising the automatic injector comprising a non-sedating antihistamine composition described herein, and a second autoinjector comprising a second housing comprising a second chamber for an epinephrine composition and a second dispensing assembly in communication with the second chamber.

Some embodiments provide methods of treating an acute allergic reaction comprising administering to a patient in need thereof an effective amount of an injectable composition of levocetirizine, pharmaceutical acceptable salt, polymorph, thereof which is substantially free from hemolytic effect to a patient in need of such treatment.

Any of the various embodiments can be designed to deliver an effective amount of cetirizine, a pharmaceutically acceptable salt or polymorph thereof, in an injection volume of from about 0.2 mL to about 10 mL. In some cases, the injection volume is about 0.5 mL to about 5 mL. In some cases, the injection volume is about 2 mL. In some cases the injection volume is about 1 mL.

In another aspect, the 90% confidence limits of a ratio of a logarithmic transformed geometric mean of $AUC_{0-INF}$ for the injectable formulation as described above to a logarithmic transformed geometric mean of $AUC_{0-INF}$ for a reference oral product of the nonsedating H1 antihistamine are 0.80 to 1.25; and/or wherein the 90% confidence limits of a ratio of a logarithmic transformed geometric mean of $AUC_{0-t}$ for the injectable formulation to a logarithmic transformed geometric mean of $AUC_{0-t}$ for the reference oral product of the nonsedating H1 antihistamine are 0.80 to 1.25.

In yet another aspect, the injectable formulation of the non-sedating antihistamine as described above has a 90% confidence interval around the difference in the reduction of at least one symptom of anaphylaxis or an acute allergic reaction to a reference injectable product, such as diphenhydramine injection, for the per protocol evaluable population, within about −30.00 to about +30.00, wherein the symptom is pruritus severity, pruritus duration, erythema, angioedema, number of urticaria areas, number of erythema areas, and/or wheezing.

In another aspect, the injectable formulation of the non-sedating antihistamine as described above is statistically superior ($p<0.05$) to a placebo in the reduction of at least one symptom of anaphylaxis or an acute allergic reaction, wherein the symptom is pruritus severity, pruritus duration, erythema, angioedema, urticaria areas, erythema areas, and/or wheezing.

In another aspect, an automatic injector designed to allow a user to self-administer a pre-measured dose of a non-sedating antihistamine composition subcutaneously or intramuscularly, comprises a housing comprising a chamber for the non-sedating antihistamine composition and a dispensing assembly in communication with the chamber, wherein the nonsedating antihistamine composition comprises an non-sedating antihistamine and a pH adjusting agent and has a pH of 3 to 9, wherein the non-sedating antihistamine comprises cetirizine, loratadine, levocetirizine, desloratadine, or fexofenadine.

In yet another aspect, a kit comprises the automatic injector comprising a nonsedating antihistamine composition as described above and a second automatic injector comprising a second housing comprising a second chamber for an epinephrine composition and a second dispensing assembly in communication with the second chamber.

DETAILED DESCRIPTION

The terms "a" and "an" do not denote a limitation of quantity, but rather denote the presence of at least one of the referenced item. The term "or" means "and/or." The terms "comprising," "having," "including," and "containing" are to be construed as open-ended terms (i.e., meaning "including, but not limited to"). Unless defined otherwise, technical and scientific terms used herein have the same meaning as is commonly understood by one of skill in the art to which this invention belongs. The endpoints of all ranges directed to the same component or property are inclusive and independently combinable.

The term "non-sedating antihistamines" represent the $2_{nd}$ and/or $3_{rd}$ generation antihistamines that are truly non-sedating and/or that are less-sedating than diphenhydramine.

"Substantially free of sedative effect" means truly non-sedating and/or significantly less sedating than the first generation antihistamines, such as diphenhydramine or hydroxyzine.

The term "Cetirizine" is (±)-[2-[4-[(4-chlorophenyl)phenylmethyl]-1-piperazinyl]ethoxy]acetic acid and includes cetirizine itself, its pharmaceutical acceptable salts such as the HCl salt etc. and its various polymorphs. "Cetirizine" is a non-sedating antihistamine. Isomers of cetirizine such as levocetirizine and dextrocetirizine are referred to specifically herein, and it is intended that "cetirizine" alone is meant to refer to the (±) form, unless indicated otherwise.

The term "pharmaceutically acceptable salt" of a compound means any salt suitable for pharmaceutical use, for example, an acid-addition salt of a compound of the invention which is sufficiently basic, for example, an acid-addition salt with, for example, an inorganic or organic acid, for example hydrochloric, hydrobromic, nitric, methansulphonic, sulphuric, phosphoric, trifluoroacetic, para-toluene sulphonic, 2-mesitylen sulphonic, citric, acetic, tartaric, fumaric, lactic, succinic, malic, malonic, maleic, 1,2-ethanedisulphonic, adipic, aspartic, benzenesulphonic, benzoic, ethanesulphonic or nicotinic acid. In addition a suitable pharmaceutically acceptable salt of a compound of the invention, is, for example, a base-addition salt of a compound of the invention which is sufficiently acidic, for example, a metal salt, for example, sodium, potassium, calcium, magnesium, zinc or aluminum, an ammonium salt, a salt with an organic base which affords a physiologically acceptable cation, which includes quaternary ammonium hydroxides, for example methylamine, ethylamine, diethylamine, trimethylamine, tert-butylamine, triethylamine, dibenzylamine, N,N-dibenzylethylamine, cyclohexylethylamine, tris-(2-hydroxyethyl)amine, hydroxyethyl diethylamine, (1R,2S)-2-hydroxyinden-1-amine, morpholine, N-methylpiperidine, N-ethylpiperidine, piperazine, methylpiperazine, adamantylamine, choline hydroxide, tetrabutylammonium hydroxide, tris-(hydroxymethyl)methylamine hydroxide, L-arginine, N-methyl D-glucamine, lysine or arginine.

"Substantially free of hemolytic potential" means Hemolysis less than 10% comparing to the positive control, DI water, as discussed below under Hemolysis Studies. In some embodiments, it means less than 5%. In some other embodiments, it means less than 2%.

The term "patient" includes human patient and/or animal patient.

"Acute allergic reaction" means an allergic condition of the immediate type (in human or animals), severe allergies/anaphylaxis, or severe allergic reaction such as allergic reactions to blood or plasma, to food, to medications, or to other allergy inducing materials. "Acute allergic reaction" ranges from urticaria to anaphylaxis. "Acute allergic reaction" includes urticaria, angioedema, erythema, wheezing, pruritus, constriction of airways, hypotension, or other issues of the immediate type, or combinations thereof. "Acute allergic reaction" differs from chronic or seasonal allergies. For example, it is very much different from seasonal and/or perennial rhinitis. They are different on treatment regimens, patient types, source of allergens, patient population, medication usage, and etc. "Acute allergic reaction" does not include seasonal and/or perennial rhinitis.

"Urticaria" includes acute urticaria and chronic idiopathic urticaria.

Acute allergic reaction is an acute multi-system severe type I hypersensitivity reaction. Pseudoanaphylaxis does not involve an allergic reaction, but is due to direct mast cell degranulation. Both anaphylaxis and pseudoanaphylaxis result in an anaphylactoid reaction and treatment for both conditions is similar. The term anaphylaxis as used herein refers to both conditions unless otherwise specified. Because definitions of anaphylaxis differ even within the medical community, this description will limit its use. Instead, it should be noted that the methods, compositions, and injectables described herein are for use in treating acute allergic reactions that present without respiratory issues or where respiratory issues are being controlled. Patient safety is always of paramount importance, and those patients presenting with respiratory issues should be treated with epinephrine concurrently with antihistamines to prevent potentially life-threatening conditions.

Oral cetirizine formulations are known and available for treatment of seasonal and perennial rhinitis. Cetirizine has never been approved for use in treating acute allergic reaction nor proposed for injectable use. Several known factors have prevented scientists from trying to make cetirizine, its salt, or polymorph, and its isomers into a parenteral injection product for the treatment and/or prevention of acute allergic reactions. These factors are:

i) Key opinion leaders in the allergy space have thought and published articles about $2^{nd}/3^{rd}$ generation antihistamines being unfeasible to make into an injection product. For example, Dr. Phillip Liberman, a well-known allergist, published an article saying that non-sedating antihistamines are not able to be given by the traditionally employed injectable route, due to in-solubility. Since then, it has been discovered that of the second and third generation antihistamines only cetirizine based compounds are freely soluble in water, that is, only compound derived from cetirizine or its isomers are soluble in water.

ii) The injectable product of cetirizine's parent molecule, hydroxyzine, is known to cause hemolysis when injected intravenously due to unacceptable hemolytic effects. In fact, the FDA now requires a label on hydroxyzine injection indicating that the injectable product can not be given intravenously. As a result, it has been thought that as a metabolite of hydroxyzine, cetirizine, and/or levocetirizine, its salts or isomers would have similar hemolytic problem as the parent compound, thus would not be suitable as an injection product.

iii) The current treatment for acute allergic reaction is to use the $1^{st}$ generation antihistamines: diphenhydramine injection or hydroxyzine intramuscular injection. Both have been on the market as the treatment standard for approximately 60 years. Specifically, diphenhydramine has been considered the "gold standard" among all generations of antihistamines. Its heavy sedation side effects were often considered advantageous sometimes for acute allergic reactions by calming and relaxing the patients, especially since many patients with this condition are children. Only the first generation antihistamines have such sedation side effect.

iv) Due to the severity of acute allergic reactions, scientists believed nothing but diphenhydramine was strong enough in efficacy to treat acute allergic reactions. When formulating second and third generation antihistamines products, scientists added an anti-inflammatory agent to the formulation. Singh et al. disclosed a combinational injectable formulation of cetirizine with an anti-inflammatory agent, Nimesulide (an NSAID), for allergic disorders namely rhinitis, bronchitis, asthma, urticaria and the like.

Surprisingly, the inventors have discovered cetirizine, out of several existing antihistamines, to be water soluble, and cetirizine was successfully formulated into a parenteral injection product, particularly for IV injection. This is true of cetirizine itself, and its isomers, particularly levocetirizine. The unique cetirizine injectable formulation disclosed herein is substantially free of hemolytic effects of hydroxyzine. The cetirizine formulations and methods of treatment disclosed herein are effective in treating acute allergic reaction (urticaria, angioedema, pruritus, erythem, wheezing, or combination thereof) in the absence of an NSAID, and without much of the sedating effect of the existing gold-standard treatments.

Cetirizine, its HCl salt or its isomer levocetirizine is a newer-generation ($2^{nd}$ or $3^{rd}$ generation) antihistamine and a metabolite of the first-generation antihistamine hydroxyzine. As such, cetirizine and its isomers and hydroxyzine are similar in structure:

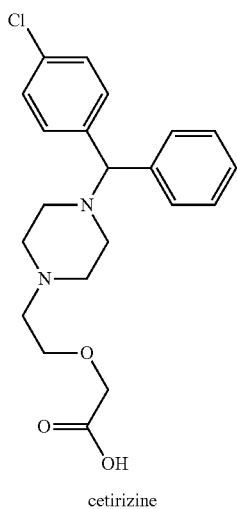

cetirizine

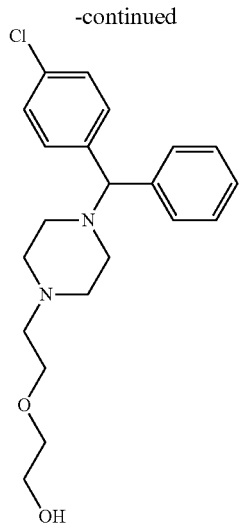

HYDROXYZINE
(±)-2-(2-{4-[(4-chlorophenyl)-phenylmethyl]piperazin-1-yl}ethoxy)ethanol Hydroxyzine is available in tablet form and as an injectable for intramuscular (IM) injection only. Hydroxyzine injectables are labeled as required by the FDA with a warning indicating that the injection is not to be given by intravenous (IV) injection, because of reported cases of hemolysis. As explained in the experiments section below, cetirizine injectable formulations in accordance with some embodiments of the invention are substantially free of hemolytic effect. Thus, unlike formulations containing the parent hydroxyzine molecule, injectable formulations of cetirizine as described herein are substantially free of the problematic event of hemolysis, and unlike hydroxyzine, they are suitable for IV injection, particularly in emergency situations. Cetirizine (salt, polymorph) injections also benefit from significantly reduced sedative effect, as well as reduced drug/drug interactions compared to hydroxyzine or diphenhydramine injections. Similar results may also be seen with isomers of cetirizine, particularly levocetirizine.

With respect to sedative effect, injections of cetirizine and its pharmaceutically acceptable salts, isomers, or polymorphs, have significantly reduced effects when compared to the first generation antihistamines, hydroxyzine IM injection and diphenhydramine injection. In the effective dose range and particularly at the proposed 10 mg daily dose, cetirizine injection is substantially free of sedative effect when compared to hydroxyzine IM injections and/or diphenhydramine injection. The sedative-free effect permits administration of cetirizine injection to specific population of patients. As discussed herein, cetirizine injectable formulations, or injections of its salt, isomer and polymorph, can be given to patients with reduced sedation, reduced fear of drug/drug interactions, reduced fear of hemolytic potential, reduced frequency of drug administration, reduced fear of additive sedative effects, reduced fear of cardiotoxicity (QT prolongation), and with reduced monitoring efforts and requirements, when compared to diphenhydramine or hydroxyzine injections.

The cetirizine injection formulations described herein are useful, for example, in the hospital or acute care settings and methods of treating acute allergic reactions with such injections. In allergic reactions, an antigen interacts with and cross-links surface IgE antibodies on mast cells and basophils. Once the mast-cellantibody-antigen complex is formed, a complicated series of events occurs that eventually leads to mast cell degranulation and the release of histamine and other chemical mediators from the mast cell or basophil. After its release, histamine can react with local or widespread tissues through histamine receptors. Histamine receptor sites, histamine-1 ($H_1$), and histamine-2 ($H_2$) have a role in acute allergic reactions. Acting on $H_1$ receptors, histamine produces pruritus, vasodilation, hypotension, flushing, headache, tachycardia, bronchoconstriction, and increased vascular permeability. Targeting $H_2$-receptor sites, histamine causes increased stomach acid production, nausea, and flushing.

Symptoms of acute allergic reactions include pruritus, erythema, angioedema, urticaria, wheezing, and etc. Exemplary patient populations for use and/or study include patients coming to emergency rooms or allergy clinics, patients with food allergies (peanuts, other nuts, sea food, etc), patients with exercise induced allergies, patients allergic to insects stings, patients with poison ivy induced allergies, etc. Additional patients include those already in the hospital experiencing drug induced allergies to: antibiotics, IV contrast media, anesthesia, aspirin/NSAIDs, opioids, chemotherapy agents, muscle relaxants, latex gloves, blood materials, etc.

Clinical signs and symptoms of acute allergic reaction are given in Table 1:

TABLE 1

| Clinical signs and symptoms of acute allergic reactions including anaphylaxis |
|---|
| Cutaneous/subcutaneous/mucosal tissue |
| Flushing, pruritus, hives (urticaria), angioedema, morbilliform rash, pilor erection<br>Pruritus of lips, tongue, and palate; edema of lips, tongue, and uvula<br>Periorbital pruritus, erythema and edema, conjunctival erythema, tearing<br>Respiratory |
| Laryngeal: pruritus and tightness in the throat, dysphagia, dysphonia and hoarseness, dry staccatocough, stridor, sensation of pruritus in the external auditory canals<br>Lung: shortness of breath, dyspnea, chest tightness, deep cough and wheezing/bronchospasm(decreased peak expiratory flow)<br>Nose: pruritus, congestion, rhinorrhea, sneezing<br>Cardiovascular |
| Hypotension<br>Feeling of faintness (near-syncope), syncope, altered mental status<br>Chest pain, dysrhythmia<br>Gastrointestinal |
| Nausea, crampy abdominal pain, vomiting (stringy mucus), diarrhea<br>Other |
| Uterine contractions in women, and aura of doom |

Urticaria is a vascular reaction of the upper dermis marked by transient, slightly elevated patches called wheals that are redder or paler than the surrounding skin; there often is severe itching. Common causes include foods, drugs, infections, and emotional stress. Urticaria is commonly referred to as "hives," and is one of the most common symptoms of acute allergic reactions. Urticaria sometimes happens as an acute urticaria, and sometimes as a chronic idiopathic urticaria.

Pruritus is a condition involving localized or general itching that is a common and distressing symptom in a variety of diseases, especially in an allergic reaction. Although usually occurring in the skin, pruritus can also occur in non-cutaneous sites such as mucous membranes. Erythema is redness of the skin, caused by congestion of the capillaries in the lower layers of the skin.

Angioedema is an uncomfortable and disfiguring type of temporary swelling especially in the lips and other parts of the mouth and throat, the eyelids, the genitals, and the hand and feet. Angioedema is life-threatening if swelling in your mouth or throat makes it difficult for you to breathe. Less often the sheer amount of swelling means that so much fluid has moved out of the blood circulation that blood pressure drops dangerously.

Wheezing is a high-pitched whistling sound produced by air flowing through narrowed breathing tubes, especially the smaller ones deep in the lung.

Erythema is redness of the skin, caused by congestion of the capillaries in the lower layers of the skin.

As mentioned above, when presenting with severe respiratory issues, the preferred first-line treatments should be used. Once those issues have abated or being controlled, or in the absence of respiratory issues, the methods and injectable cetirizine (salt or isomer) described herein may be used.

The methods and injectables described herein address the limitations of the current treatments employing the injections of first generation antihistamines, such as hydroxyzine and diphenhydramine.

In accordance with some embodiments, the invention provides an injectable solution comprising cetirizine or a pharmaceutically acceptable salt, isomer, polymorph, thereof. The injectable is suitable for intramuscular or intravenous injection. In some embodiments, the injection is particularly suitable for intravenous injection.

Parenteral injectable formulations may be in unit dose form in ampoules, small volume parenteral (SVP) vials, large volume parenterals (SVP), pre-filled syringes, small volume infusion or in multi-dose containers. The compositions are suspensions or solutions and may contain formulatory agents such as preserving, wetting, buffering, emulsifying or suspending, stabilizing and/or dispersing agents. Alternatively, the ratio, type, and varieties of the ingredients, active and in-actives, are studied to reach an optimal balance, before use with a suitable vehicle, e.g., sterile, pyrogen-free water. Particular embodiments are contemplated that are substantially free of buffers, stabilizers, and/or preservatives, while still preserve the formulation's chemical stability, pH value, and product sterility.

Parenteral injectable formulations are typically aqueous solutions which may contain excipients such as salts, carbohydrates and buffering agents (preferably at a pH of from 3 to 9.5). Some embodiments have a pH of about 5.5+/−1.0. Additional embodiments are substantially buffer free.

In one embodiment, the injectable compositions contain a solution of cetirizine or a pharmaceutically acceptable salt, isomer, polymorph, thereof in an aqueous solvent combined with pH adjusting agents having a pH of about 5.5+/−1.0 and least one isotonicity agent. A water-insoluble inert gas may be carefully bubbled through the solvent to remove oxygen from the medium. Optionally the compositions contain at least one preservative and/or at least one solubility enhancing agent and/or at least one stabilizing agent. In some embodiments, the compositon is substantially free of stabilizing agents and preservatives.

In one embodiment, the quantity of cetirizine or salt, isomer, polymorph, thereof in the injection formulation is 1-20 mg per milliliter of liquid, preferably 2-15 mg, more preferably about 2.5-10 mg per milliliter of liquid.

In another embodiment, the composition described herein optionally further comprises a second active agent as well as cetirizine. In one embodiment, the second active agent is an H2 receptor antagonist, such as ranitidine or cimetidine. In another embodiment, the second active agent is epinephrine.

In yet another embodiment, the second active agent comprises at least one steroid, such as methylprednisolone or prednisolone. In one embodiment, the methods disclosed herein further comprise administering a second active agent comprising ranitidine, cimetidine, epinephrine, methylprednisolone, prednisolone, or a combination thereof. The second active agent is not an NSAID.

In some embodiments, the injectable comprises a single dose pH adjusted (about pH 5.5+/−1.0) solution having an effective amount of cetirizine or a pharmaceutically acceptable salt, isomer, polymorph, thereof for treating symptoms of acute allergic reaction; a tonicity agent for adjusting osmolality to about physiological osmolality; optional pH adjusting reagents; and sterile water for injection.

The single dose may be from about 0.2 mL to about 10 mL in total injection volume, and may take the form of a small volume parenteral (SVP) injection. In some embodiments, the total injection volume is about 0.5 mL to about 5 mL. In still others, the total injection volume is about 2 mL. In other embodiments, the total injection volume is about 1 mL. A 1 mL dose is well suited to an injection because it is easily introduced. Single dosage SVP vials provide ease of storage, measurement and dosing, particularly in a hectic emergency situation.

Cetirizine or a pharmaceutically acceptable salt, isomer, polymorph, thereof, will be present in an amount effective to treat acute allergic reaction symptoms, about 1 mg to about 20 mg per dose. Adult dosages will be approximately 10 mg per dose. Given the volume sizes, cetirizine or a pharmaceutically acceptable salt, polymorph, thereof will be present at about 0.1% to about 2% w/v. In some embodiments, cetirizine or a pharmaceutically acceptable salt, polymorph, thereof will be present at about 0.2% to about 1.5% w/v. In some embodiments, cetirizine or a pharmaceutically acceptable salt, polymorph thereof will be present at about 0.25% to about 1% w/v. In some embodiments, cetirizine or a pharmaceutically acceptable salt, polymorph thereof will be present at about 0.5% to about 1% w/v. In a 1 mL dose, a suitable dose is about 1% w/v of cetirizine or a pharmaceutically acceptable salt, isomer, polymorph, thereof.

Tonicity agents are sometimes present. The term "tonicity agent" refers to a pharmaceutically acceptable excipient that makes the solution compatible with blood. Suitable tonicity agents include glycerin, lactose, mannitol, dextrose, sodium chloride, sodium sulfate, sorbitol and the like. Preferred tonicity agents include mannitol, sorbitol, lactose and sodium chloride and combinations thereof, and most particularly, sodium chloride. The tonicity agent is added to the injectable to achieve substantially physiological osmolality for injection.

Physiological osmolality, as used herein, is about 255 mOsm/kg to about 315 mOsm/kg. An injectable having an osmolality in this range is said to be isotonic. Hypertonic and hypotonic solutions both present complications and undesirable effects when injected. The injectables described herein are isotonic to minimize or avoid such effects. Since osmolality is the measure of particles in a solution, every component added to the injectable affects the osmolality, thus, adjusting to a final osmolality is complicated, particularly when also adjusting the pH, as addition of the tonicity agent may affect pH and addition of the pH adjusting reagents will affect tonicity.

Optional pH adjusting reagents include acids and bases, such as but not limited to dilute HCl and NaOH. An acid may be added to lower the pH, while the base is added to raise pH. In some instances one or both an acid and a base may be used. In some embodiments, the pH adjusting reagents are chosen to complement the tonicity agent to provide similar ions when in solution. For example, when NaCl is used as a tonicity agent, HCl and/or NaOH may be used as the pH adjusting reagents.

Sterile water for injection is used to increase the volume of the injectable to the desired level.

Injectables in accordance with some embodiments of the invention comprise:
 a total injection volume of about 0.2 mL to about 10 mL;
 an effective amount of cetirizine or a pharmaceutically acceptable salt, polymorph, thereof, or about 1 mg to about 20 mg;
 a tonicity agent in an amount to achieve physiological osmolality;
 a pH adjusting reagent such as an acid and/or a base to adjust pH to about 5.5+/−1.0;
 q.s. sterile water for injection.

In some embodiments, the total injection volume is about 0.5 mL to about 5 mL. For ease of measurement, storage and dosage measurement, the injectable is provided in a single dosage form. In some instances, the total injection volume is 1 mL. The total injection volume contains an effective amount of cetirizine. Smaller volumes therefore will have a higher concentration of cetirizine. For example, a dose of about 10 mg of cetirizine in a 1 mL total volume injectable is about 1% w/v with respect to cetirizine, salt, isomer or polymorph.

Effective doses of cetirizine or a pharmaceutically acceptable salt, isomer, polymorph, thereof are about 1 mg to about 20 mg daily. An adult dose of about 10 mg per day is believed to be sufficient via the intravenous route, even for acute allergic reactions. As with other medications, greater or smaller doses may be employed based upon a number of factors, including but not limited to age, weight, or severity of the condition. In some embodiments, an isomer of cetirizine may be used. Particularly, levocetirizine may be used in about half of the amounts of cetirizine.

The tonicity agent, such as NaCl, is employed to achieve an isotonic solution. Isotonic solutions for injection have an osmolality roughly equivalent to physiological osmalality, which as used herein is about 255 mOsm/kg to about 315 mOsm/kg. In the exemplary 1% w/v cetirizine HCl 1 mL injectable, it has been found that about 0.65% NaCl yields an osmolality within the physiological range (when the solution is pH adjusted to pH about 5.5+/−1.0). Other concentrations of NaCl resulted in either undesirable hypertonic or hypotonic solutions.

In some embodiments, the formulation is substantially free of buffers, contrary to most injectable formulations. Surprisingly, this unique buffer free formulation described herein maintained its pH values upon heat storage at 60° C. and maintained its stability. The benefit of this buffer free formulation allows immediate and ease dilution by the blood flow upon injection to the patient's blood circulation. In some embodiments, the formulation is substantially free of preservatives. As discussed below, an exemplary formulation was stable during an accelerated stability test for up to 5 days at 60° C. Thus, the injectable is stable and has a long shelf life.

Additional components, such as active agents, excipients, diluents, buffers, preservatives, etc. may be employed, so long as the injectable remains isotonic and stable. Any suitable additional active agent could optionally be incorporated into the injectable, provided that the additional active agent is not an NSAID.

As noted above, H2 antagonists, such as ranitidine or cimetidine are suitable additional active agents. Other possibilities include, but are not limited to famotidine and nizatidine.

One exemplary injectable in accordance with some embodiments of the invention comprises:
  a 1 mL total injection volume;
  about 10 mg cetirizine or a pharmaceutically acceptable salt, polymorph, thereof;
  about 6.5 mg NaCl;
  HCl and/or NaOH to pH 5.5+/−1.0; and
  q.s. sterile water for injection.

In some embodiments, the formulation is substantially free of buffers. In some embodiments, the formulation is substantially free of preservatives.

In some embodiments, an isomer of cetirizine may be used. Particularly, levocetirizine may be used in about half of the amounts.

Injectables in accordance with some embodiments of the invention consist essentially of:
  a total injection volume of about 0.5 mL to about 5 mL;
  an effective amount of cetirizine, or a pharmaceutically acceptable salt, polymorph, thereof, or about 1 mg to about 20 mg cetirizine;
  a tonicity agent in an amount to achieve physiological osmolality;
  a pH adjusting reagent such as an acid and/or a base to adjust pH to about 3-9, preferably about 5.5+/−1.0; and q.s. sterile water for injection.

In some embodiments, an isomer of cetirizine may be used. Particularly, levocetirizine may be used in about half of the amounts.

One exemplary injectable in accordance with some embodiments of the invention consists essentially of:
  a 1 mL total injection volume;
  about 10 mg cetirizine, or a pharmaceutically acceptable salt, polymorph, thereof;
  about 6.5 mg NaCl;
  HCl and/or NaOH to pH about 5.5+/−1.0; and
  q.s. sterile water for injection.

In some embodiments, an isomer of cetirizine may be used. Particularly, levocetirizine may be used in half of the amounts used in cetirizine formulations.

In some embodiments, the formulation is substantially free any additional components.

One embodiment provides an injectable formulation comprising:

| Component | % w/v | Mg/mL |
|---|---|---|
| Cetirizine HCl, EP | 1.00 | 10.00 |
| Sodium chloride, USP | 0.65 | 6.5 |
| Sodium hydroxide (pellets) NF | q.s. to adjust pH to about 5.5 +/− 1.0 | q.s. to adjust pH to about 5.5 +/− 1.0 |
| Diluted HCl, NF | q.s. to adjust pH to about 5.5 +/− 1.0 | q.s. to adjust pH to about 5.5 +/− 1.0 |
| Water for injection, USP | q.s. to 100% | q.s. to 1.00 mL |

Some embodiments of the invention provide methods for treating acute allergic reaction or one or more symptom of acute allergic reaction. In accordance with some embodiments of the invention, the method of treatment comprises administering to a patient suffering from an acute allergic reaction a parenteral, preferably an injection of a formulation as set forth herein. The acute allergic reaction to be treated may include, but is not limited to urticaria, angiodema, pruritis, erythema, wheezing or combinations thereof.

Some embodiments include a method of treating an acute allergic reaction in a patient in need thereof by administering a formulation comprising:
  a total injection volume of about 0.2 mL to about 10 mL;
  an effective amount of cetirizine, or a pharmaceutically acceptable salt, polymorph, thereof, or about 1 mg to about 20 mg;
  a tonicity agent in an amount to achieve physiological osmolality;
  a pH adjusting reagent such as an acid and/or a base to adjust pH to about 3-9, preferably about 5.5+/−1.0; and q.s. sterile water for injection.

Sterilization and fill into containers, or fill into containers and sterilization.

In some embodiments, an isomer of cetirizine may be used. Particularly, levocetirizine may be used in half of the amounts.

Currently, the injections of first generation antihistamines (diphenhydramine and hydroxyzine) are the preferred and only course of treatment in treating acute allergic reactions. They, however, are know to have side effects of potential cardio toxicity (QT prolongation), severe sedation, anti-cholinergic effect, potential of drug/drug interaction, and short half-life which requires 3-4 doses a day. Cardio toxicity presents a huge safety concern, and the sedation side effect causes significantly inconvenience and discomfort for patients. The sedating side effect presents a safety concern when patients have to drive home themselves after being discharged from the emergency room. The sedating side effect also interferes with neurological exams for patients who are in need such exams in the hospital. Patients with allergic reactions to opioids are treated with diphenhydramine injections. This causes a dangerous additive effect in sedation. Diphenhydramine's QT prolongation is potentially life threatening and could lead to hospital admission. Sometimes acute allergic patients come to the ER and already took a few diphenhydramine tablets. ER doctors then put the patients on injection diphenhydramine as a standard procedure. This accumulated diphenhydramine concentration could cause cardiac arrest leading to hospital admission. QT prolongation is worsened by drug/drug interaction. In ICUs, diphenhydramine injection is frequently used as a preventive measure to desensitize antibiotics (antibiotics have a high incidence for drug induced allergic shock). In ICUs, patients are normally on multiple medications, and the potential drug/drug interaction and liver enzyme P450 inhibition leading to cardiac arrest due to QT prolongation is extremely dangerous. Diphenhydramine injection is commonly used together with blood transfusion to prevent allergic reactions to blood or plasma. Diphenhydramine injection is often used to treat anesthesia induced allergies in the operating room. It takes longer for patients to awake from the anesthesia when diphenhydramine injection is co-used. Therefore there is a great advantage and unmet medical need for a non-sedating antihistamine injection with longer duration of action, without QT prolongation, and without hemolysis Regardless, the concern for sedation alone is significant, although sedation maybe beneficial in some specific types of patients. Patients who become overly sedated are more prone to falls and injury, and require monitoring and extended hospital stays or delayed discharge. Accordingly, some embodiments of the invention provide methods for treating acute allergic reaction in patient requiring no further sedation which comprises injecting into a patient in need of such treatment, a cetirizine formulation as described herein. Particularly, the method of treating acute allergic reaction in a patient requiring no further sedation comprises the steps of administering such a formulation to the patient. In some embodiment, no additional monitoring of the patient is required. In some embodiments, patient monitoring continues only with respect to a reduction of allergic symptoms. That is, because of the reduced sedative effect, the patient need not be monitored for sedation as would be the case with traditional treatments. In the case where the patient is initially unsedated, no monitoring for sedation need take place. In the case where the patient was initially sedated, no additional monitoring need take place.

In an emergency situation such as an emergency department, the hospital staff might not have access to the medical history of the patient and may not be able to determine what if any medications the patient is on. Thus, some embodiments of the invention provide methods of treating acute allergic reaction by administering formulation described herein without regard for the patient recent medication intake history and/or with reduced likelihood of drug/drug interactions or possible drug overdose or under-dose.

Traditional antihistamines such as hyroxyzine and diphenhydramine have potential major, moderate, and minor interactions with a large number of drugs, and are cautioned in the presence of other disease states. Thus, when administering these first generation antihistimines without full or reliable patient history there is always a risk that patient will have an adverse reaction. To minimize these potential situations, some embodiments provide for treating acute allergic reaction without regard for the patient's recent medication intake history. This can be done, because cetirizine, or levocetirizine, salt, isomer, or polymorph, particularly at the effective IV doses, has significantly reduced sedative effect and drug interactions when compared to diphenhydramine and hydroxyzine. When compared to the first generation antihistimines, cetirizine has fewer potential drug/drug interactions. At least one source indicates the following:

|  | Major | Moderate | Minor | Disease state interaction |
|---|---|---|---|---|
| Hydroxyzine http://www.drugs.com/ drug-interactions/ hydroxyzine.html | 17 | 622 | 6 | Anti-cholinergic effects, Asthma/ COPD; Cardiovascular; Renal/Liver disease |
| Diphenhydramine http://www.drugs.com/ drug-interactions/ diphenhydramine.html | 26 | 590 | 5 | Anti-cholinergic effects, Asthma/COPD; Cardiovascular; Renal/Liver disease |
| Cetirizine (oral) http://www.drugs.com/ disease-interactions/ cetirizine.html | 0 | 568 | 5 | Renal/ Liver Disease |

Although a full patient history is always preferable, sometimes it is difficult or impossible to obtain the history under emergency setting. Some embodiments of the methods herein account for those situations, where administration occurs in the absence of the patient recent medication intake history. Even in such situations, the medical care worker is informed and assured that fewer possible undesirable interactions will occur, compared to diphenhydramine and/or hydroxyzine.

Accordingly, some embodiments of the invention provide a method of treating an acute allergic reaction while minimizing drug interactions comprising:

identifying a patient potentially suffering from an acute allergic reaction;

administering, to the identified patient, an injection of an amount of cetirizine, or a pharmaceutically acceptable salt, or polymorph, thereof without regard for the drug and/or medical history of the identified patient; and informing the patient or a medical care worker that the injection of cetirizine or levocetirizine or a pharmaceutically acceptable salt, isomer, polymorph, is unlikely to produce, or be subject to metabolic drug/drug interactions.

In some embodiments, an isomer of cetirizine may be used. Particularly, levocetirizine may be used in half of the amounts.

As with all methods in accordance with various embodiments of the invention, the administering step is carried out as soon after suspicion of acute allergic reaction as possible. Potential exacerbation of symptoms can be avoided by quickly identifying a patient as having an acute allergic reaction and the quickly beginning treatment.

In many instances, a patient may have already taken an oral antihistamine before going to the hospital. In these instances, such a patient could be subjected to a dangerous overdose of antihistamine. The overdose, in the case of sedative antihistamines, would lead to further sedation which could lead to depressed respiration and other issues. In the case of diphenhydramine, an overdose can lead to QT prolongation which has significant cardiac risks.

Thus, some embodiments of the invention are directed to methods to be applied when a patient has been or is believed to have been administered a first generation antihistamine prior to the identifying step. In such instances, a second dose of a first generation antihistamine would cause undesired and potentially dangerous further sedation, but also might result in antihistamine overdose, which could result in cardiac issues, such as QT prolongation. The use of the methods described herein avoids this potentially dangerous situation.

Although the benefit of these methods is clear where the patient's history is uncertain, the same benefits can be had where the patient's history is known. For example, in some embodiments, the administration is performed with full knowledge of the patient's history including current use of first generation antihistamine. In such instances, where e.g. diphenhydramine was previously administered, the care taker would know that the option of administering diphenhydramine was not available, and that administering cetirizine according to the methods herein would provide a way to treat the patient's acute allergic reaction regardless of interactions without significantly altering the drug interaction profile.

In accordance with some embodiments of the invention, a method of treating an acute allergic reaction while minimizing drug interactions or possible antihistamine overdose, comprises:

identifying a patient potentially suffering from an acute allergic reaction or symptoms of an acute allergic reaction;

administering, to the identified patient, an injection of an amount of cetirizine or a pharmaceutically acceptable salt, or polymorph thereof without regard for the drug history of said identified patient.

In some embodiments, an isomer of cetirizine may be used. Particularly, levocetirizine may be used in about half of the amounts.

As will be appreciated, the sooner the acute allergic reaction can be treated, the better. Accordingly, in some embodiments, the injection is administered as soon as possible, and if possible upon the first suspicion of acute allergic reaction. The treatment should begin within 12 hours of exposure to the allergen if possible. If possible, treatment within 6 hours or less would be even better.

In some instances, due to the emergency nature of the administration, the injection in accordance with the invention can be administered the complete absence of the patient recent medicine intake history. Because cetirizine has fewer interactions and side effects, it can be administered with reduced liability, and can be administered quickly, even before a full patient history is available. This can be quite important if the patient is unconscious or otherwise unable to talk, or must be prepared for other procedures. Of course, where possible, a full or partial patient history is always helpful in treating a patient, and the treatment can begin in some situations after a history has been taken. There are, however, some situations where the history is unavailable.

In other situations, the history is known, and directs against administration of a sedating first generation antihistamine. For example, the treatment methods described herein are particularly well-suited when the patient has taken or is believed to have taken an early dose of a first generation antihistamine, or has been on many other medications In such instances, a second emergency dose could prove detrimental. In such instances, an injection in accordance with the invention herein could be administered.

Because of the highly sedative effect, the large number of drug interactions, and other reasons, several patient groups are unsuitable for treatment with first generation antihistamines, particularly diphenhydramine. For example, patients requiring no sedation such as those who could otherwise resume normal activity, patients who are already sedated, the elderly, Ob-gyn patients, patients who require CNS or cognitive evaluation, or those otherwise at risk of falling, etc. Sedated patients require increased monitoring and longer stays, thus, from the caretaker point of view, significant resources can be saved through reduced monitoring and earlier discharge when a patient can be given a non-sedating treatment. In other cases, such as with the elderly or pregnant women, the danger of falling and creating other injury far outweighs the benefit of administering the drug.

Thus, a method of treating symptoms of acute allergic reaction in a patient for whom a first generation antihistamine is unsuitable, comprises identifying such a patient, and injecting, into a patient in need of such treatment, an injectable solution of cetirizine, levocetirizine or a pharmaceutically acceptable salt, isomer, polymorph, thereof as described herein. In some embodiments, the effective dose of cetirizine is about 10 mg, and levocetirizine is 5 mg. This method of treating acute allergic reaction benefits from the fact that the patient can be monitored until a reduction of allergic symptoms is achieved. The method does not include nor need additional monitoring for sedation or additive effects of sedation. By additional monitoring for sedation it is meant that if a patient is already sedated, they should be monitored accordingly, but no increased monitoring is necessary. For patients who are initially unsedated, no monitoring for sedation is required, and the patient, absent other symptoms or conditions, may be discharged without fear of undesired sedation. Quicker and safer discharges are therefore possible.

Exemplary patients for whom first generation antihistamine may be undesirable or unsuitable includes ambulatory elderly patients, OB-gyn patients, sedated patients, patients with cardiac risk, patients with multiple attacks of acute allergic reactions within a few hours, patients on multiple drugs, patients with unknown drug profiles, and/or those for whom sedation is undesirable. Although in some case, sedation may be desirable to control the patient, in many cases, sedation is unwanted and undesirable.

First generation antihistimines (diphenhydramine and hydroxyzine) have a short half life, and require frequent dosing (every 4 to 6 hours) to maintain effectiveness. The cetirizine based injection described herein has a relatively long half life with extended anti-inflammatory effect suitable for a once daily administration. Accordingly, a method of treating an acute allergic reaction comprises daily administering to a patient in need thereof an injectable formulation of cetirizine, or levocetirizine, salt, isomer, or polymorph, as described herein.

Urticaria (hives) is perhaps the most common acute allergic reaction as such, some methods of the invention are directed specifically towards treatment of acute urticaria or chronic idiopathic urticaria. For example, a method for treating uticaria comprises administering to a patient in need of such treatment of an injection composition of cetirizine, levocetirizine or a pharmaceutically acceptable salt, isomer, polymorph thereof in an amount effective to treat said urticaria while minimizing sedation and reducing hemolytic potential. One exemplary method includes administering to a patient in need of such treatment an injection comprising a 1 mL total injection volume; about 10 mg cetirizine (or 5 mg levocetirizine) or a pharmaceutically acceptable salt, isomer, polymorph, thereof; about 6.5 mg NaCl; HCl and/or NaOH to pH 5.5+/−1.0; and q.s. sterile water for injection.

Some embodiments of the invention provide methods of treating an acute allergic reaction comprising administering an IV formulation of a hydroxyzine metabolite, such as cetirizine to a patient in need of such treatment, wherein the treatment is substantially free from hemolytic effect. Analysis was performed to study the hemolytic effect of the present invention which was proven substantially free of hemolytic effect. In some embodiments, an isomer of cetirizine may be used. Particularly, levocetirizine may be used in about half of the amounts of cetirizine In some embodiments, the hydroxyzine metabolite is substantially free of hydroxyzine. In some embodiments, hydroxyzine is present at less than about 0.1% of the metabolite. In some embodiments, hydroxyzine is present at less than about 0.05% of the metabolite. In some embodiments, hydroxyzine is present in less than about 0.01% of the metabolite.

Due to the fast onset of acute allergic reactions, often patients do not have sufficient time to reach medical care facilities for treatment. In this life and death situation, it is important that patients administer medications to themselves immediately. Accordingly, there is a need in the art to develop injectable formulations and optionally self operated and ready to use auto injector products, needle or needleless, providing a rapid delivery of the injectable non-sedating antihistamine formulation. For animals, the animal owner can administer the said auto-injector to the animal without being at the veterinarian's facility.

An automatic injector or auto-injector is a device designed to allow a user to selfadminister a pre-measured dose of a medicament composition subcutaneously or intramuscularly, usually in an emergency situation. A typical auto-injector has a housing, inside of which is a cartridge. The cartridge has one or several chambers containing medicament compositions or components thereof and is in communication with a dispensing assembly such as needle assembly. The cartridge can hold either a pre-mixed liquid medicament or a solid medicament and a liquid that are mixed prior to injection. The housing carries an actuation assembly with a stored energy source, for example, a compressed spring. Activation of the actuation assembly causes a sequence of movements, whereby the needle extends from the autoinjector into the user so that the medicament compound is then forced through the needle and into the user. After delivery of the dose of medicament into the injection site, the needle remains in an extended position or in a hidden position. If the auto-injector is of the type designed to carry plural components of the medicament composition in separate, sealed compartments, structure may be included that forces the components to mix when the actuation assembly is activated.

Autoinjectors for antihistamine administration do not exist. Advantages of the use of auto-injectors to dispense non-sedating (second and third generation) antihistamines for the treatment of severe allergic reactions include availability for emergency treatment, precise dosing, portability, readiness for use, rapid intramuscular or subcutaneous administration, administration through clothing and protective wear, and rapid self-administration. The advantages of this invention also include its non-cardiotoxicity (no QT prolongation), and nonsedating. Unlike the current highly sedating diphenhydramine injections, the non-sedating feature of this invention allows patients to be alert enough to drive to the hospital or emergency care facility after they self administer the nonsedating antihistamine injection via an auto injector.

sured to determine which API-salt formulations were isotonic after compounding. The formulations with salt content at 0.8% and 0.9% osmolalities exceeded the isotonic osmolality range of ~250-310 mOSm/kg $H_2O$ with measurements of 331 and 358 respectively. For the formulations with salt content at 0.65% and 0.7%, osmolalities were within the isotonic range with measurements of 285 and 298 respectively. After pH adjustment with added NaOH or HCL solutions, only the formulation with 0.65% sodium chloride achieved the desired osmolality. All of the formulations were clear and colorless in appearance and had a HPLC % purity of the cetirizine >99.7% and assay content >95%.

Reagents used in the study were: Sodium Chloride, USP-FCC, Mallinckrodt, Lot No. 7532Y51617, SLPL No. R-04-046. Hydrochloric Acid, ACS grade (37%), GFS Chemicals, Lot No. P892637, SLPL No. R-08-068. Sodium Hydroxide, ACS grade, Mallinckrodt, Lot No. C42K50, SLPL No. R-07-036 Water for Injection, USP grade.

| Cetirizine Dihydrochloride | | | | | | |
|---|---|---|---|---|---|---|
| Sample | Appearance | pH | Osmolality (mOsm/kg $H_2O$) | Wt. of API (mg/10 mL) | Assay % w/w Content | % Total Impurities (a/a) |
| API, 0.65% NaCl | Clear, colorless solution | 5.4 | 285 | 101.7 | 97.7 | 0.20 |
| API, 0.7% NaCl | Clear, colorless solution | 5.5 | 298 | 101.7 | 97.5 | 0.27 |
| API, 0.8% NaCl | Clear, colorless solution | 5.2 | 331 | 102.3 | 99.3 | 0.22 |
| API, 0.9% NaCl | Clear, colorless solution | 4.9 | 358 | 100.6 | 100.8 | 0.21 |
| API, 0.65% NaCl | Clear, colorless solution | 4.6 | 282 | 101.2 | 98.3 | 0.17 |
| API, 0.65% NaCl | Clear, colorless solution | 5.3 | 287 | 101.4 | 95.5* | 0.16 |

*Note: There was a dilution error (final dilution volume of the formulation was slightly higher than the required dilution) during the HPLC testing of the last formulation leading to a slightly lower assay value (95.5%). The last two formulations were re-prepared to verify qualitatively the first formulation (the 0.65% NaCl formulation) over the pH range of 4.5-6.5. The last formulation was repeated, and was freshly prepared and tested in triplicates to confirm the assay results. This formulation was tested with a fresh standard with due diligence to be accurate as possible to reflect the quantitative assay of the formulation. The average Assay content (% w/w) of the three samples was 99.8% (99.5-100.0) as the table below. After 1 week of stability testing at accelerated temperature of 60° C., the impurity and content levels of the formulation described below did not change, nor did the pH and osmolality values.

| Sample | Appearance | pH | Osmolality (mOsm/kg $H_2O$) | Wt. of API (mg/50 mL) | Avg. Assay % w/w Content | Avg. % Total Impurities (a/a) |
|---|---|---|---|---|---|---|
| API, 0.65% NaCl | Clear, colorless solution | 5.2 | 284 | 500.60 | 99.8 | 0.15 |

In another embodiment, a kit comprises the automatic injector comprising a nonsedating antihistamine composition as described above, and a second automatic injector comprising a second housing comprising a second chamber for an epinephrine composition and a second dispensing assembly in communication with the second chamber.
Formulation Study Formulation development work was performed by creating a series of solutions with different sodium chloride amounts (0.65%, 0.70%, 0.8% and 0.9%) to achieve an isotonic solution after addition of the cetirizine API. The Cetirizine hydrochloride (sometimes it is also termed as: cetirizine dihydrochloride) API was added to each salt solution at a dosage of ~10 mg/mL (see table below for actual weights) and pH adjustment (range 4.5-6.5) was made using 1N sodium hydroxide and 1% hydrochloric acid. Osmolality was mea- It was concluded that the cetirizine HCl injection formulation with 0.65% salt content gave the best result in pH, osmolality and drug stability. The total impurities seen in the data were carried from the original API (0.2-0.3% a/a). No new impurities were generated in the formulation and stability.
Hemolysis Study The hemolysis study was conducted on cetirizine injection 10 mg/mL at 4 various concentrations equivalent upto 40 times of the human Cmax concentration to assess its hemolytic potential in human blood, by using saline as the vehicle and negative control, and De-ionized or sterile water for injection as the positive control. The test article (cetirizine injection 10 mg/mL—formulation of the present invention) was prepared on the day of the study at room temperature by first preparing a stock solution as follows:

| Composition of Cetirizine HCl Injection | | |
|---|---|---|
| Component | % Composition | mg/mL |
| Cetirizine hydrochloride, EP | 1.00 | 10.00 |
| Sodium chloride, USP | 0.65 | 6.500 |
| Water for Injection, USP | q.s. to 100% | q.s. to 1.00 mL |

Adjust pH to 5.3 using sodium hydroxide or dilute hydrochloric acid as needed.

(Osmolality=255-315 mOsm/kg; pH=4.5-6.0)

The stock solution was then diluted using 0.9% saline solution to the following concentrations: 0.5, 2, 10, and 20 µg/mL (see rationale below for concentration choices).

On the day of the study, duplicate 1 mL samples of each study solution, at various locations of the container, including the vehicle control article, were obtained for analysis.

Test System Description
  Identity: Blood
  Species: Human
  Total Number: 4
  Gender: 2 male and 2 female
  Age Range: Adult (18 yrs or older)
  Body Weight Range: A minimum of 110 lb
  Source: Healthy volunteer from Calvert Rationale for Choice of Species and Number of Donors The test article is being developed for use in humans. Release of hemoglobin from lysed red blood cells has been shown to be an effective method for determining the hemolytic potential of test materials following direct contact with blood (O'Leary, et. al., 1969). The total number of donors used in this study is sufficient to provide data on the variation of responses between individuals.

Prestudy Health Screen and Selection Criteria

The health status of the human donors was determined. The donors were apparently healthy (absence of any known health conditions or diseases) volunteers. The donors were non-smokers who had not taken prescription drugs in the past week, or any non-prescription drugs in the last 24 hours, and had not consumed any alcohol in the last 24 hours Test Article Administration
  Dosing Route: in vitro
  Frequency: Once
  Procedure: Test article dosing solutions (4 concentrations) and the vehicle and positive control was mixed with 0.04 mL of the blood substrates.

Justification for Route, Dose Levels and Dosing Schedule

Dose levels were selected based on the following projected human Cmax:

i) When 10 mg cetirizine injection is given as an iv bolus, an average human is assumed to be 70 kg, with 5 L blood in general circulation, resulting in the Cmax at 10 mg/5 L, equivalent to 2 µg/mL (Cmax1)

ii) Another method of projection was to use pharmacokinetic modeling:

Oral cetirizine 10 mg gives a Cmax of 311 ng/mL, and an AUC of 4508 ng·hr/mL. The reported absolute bioavailability for the oral cetirizine 10 mg is between 75-90%. Under the worst case situation, absolute bioavailability of 75% was taken into the calculation. Cmax of the IV cetirizine injection (10 mg/mL) was calculated, using pharmacokinetic modeling, to be approximately at 480 ng/mL. The Cmax was then rounded to 500 ng/mL (0.5 µg/mL—Cmax2) for ease of calculation.

Based on these assumptions:

20 µg/mL test solution concentration is equivalent to 10×Cmax1 and 40×Cmax2.

10 µg/mL test solution concentration is equivalent to 5×Cmax1 and 20×Cmax2.

2 µg/mL test solution concentration is equivalent to 1×Cmax1 and 4×Cmax2.

0.5 µg/mL test solution concentration is equivalent to 0.25×Cmax1 and 1×Cmax2.

These 4 concentrations were used as the final concentrations for the test article.

Assay

Blood Sample Collection

Blood samples from 4 healthy human volunteers were collected in heparinized tubes. The blood samples were maintained at room temperature and tested on the day collected.

Preparation of Blood Substrate:

A series of dilutions of each blood sample was prepared in saline. 0.04 ml of each dilution was added to 2 ml of de-ionized water. Samples were incubated for 10 minutes at 37±2° C. and centrifuged at approximately 100×g for about 10 minutes at room temperature. The dilution suitable for each individual blood sample which results in an optical density (OD) of the supernatant between 0.8 and 1.2 at 540 nm was used for the assay (referred to as blood substrate). (referred to as blood substrate).

Main Study

The assay of each dose formulation, vehicle control, positive control and negative control was performed in duplicate in glass tubes as follows:

| Tube | Blood Substrate(0.04 ml) | Treatment (2 ml) | Dose (µg/ml) |
|---|---|---|---|
| 1[a] | Human 1 | Vehicle | — |
| 2[b] | Human 1 | Water | — |
| 4 | Human 1 | Test Article | 0.5 µg/ml |
| 5 | Human 1 | Test Article | 2 µg/ml |
| 6 | Human 1 | Test Article | 10 µg/ml |
| 7 | Human 1 | Test Article | 20 µg/ml |
| 8[a] | Human 2 | Vehicle | — |
| 9[b] | Human 2 | Water | — |
| 11 | Human 2 | Test Article | 0.5 µg/ml |
| 12 | Human 2 | Test Article | 2 µg/ml |
| 13 | Human 2 | Test Article | 10 µg/ml |
| 14 | Human 2 | Test Article | 20 µg/ml |
| 15[a] | Human 3 | Vehicle | — |
| 16[b] | Human 3 | Water | — |
| 18 | Human 3 | Test Article | 0.5 µg/ml |
| 19 | Human 3 | Test Article | 2 µg/ml |
| 20 | Human 3 | Test Article | 10 µg/ml |
| 21 | Human 3 | Test Article | 20 µg/ml |
| 22[a] | Human 4 | Vehicle | — |
| 23[b] | Human 4 | Water | — |
| 25 | Human 4 | Test Article | 0.5 µg/ml |
| 26 | Human 4 | Test Article | 2 µg/ml |
| 27 | Human 4 | Test Article | 10 µg/ml |
| 28 | Human 4 | Test Article | 20 µg/ml |
| 30 | Saline | Test Article | 0.5 µg/ml |
| 31 | Saline | Test Article | 2 µg/ml |
| 32 | Saline | Test Article | 10 µg/ml |
| 33 | Saline | Test Article | 20 µg/ml |

[a]= negative control and vehicle control for hemolysis
[b]= positive control for hemolysis Tubes were gently mixed and incubated without agitation for 1 hours at 37° C.±2°. After incubation, the tubes were centrifuged for 10 minutes at approximately 100×g at room temperature (15 to 30° C.). The amount of hemoglobin in the supernatant of each sample was analyzed spectrophotometrically at 540 nm.

Data Collection and Analysis

All data were manually collected except for the data generated by the spectrophotometer (Shimadzu).

The percent hemolysis was determined by the formula:

$$\% \text{ Hemolysis} = \frac{\text{Abs. of TA w/blood} - \text{Abs. of saline w/blood} - \text{Abs. of TA in saline}}{\text{Abs of water w/blood} - \text{Abs. of saline w/blood}} \times 100$$

The percent hemolysis of water plus blood is 100%. Saline is the negative control. Hemolysis≦10% is considered insignificant and free of hemolysis by industry standard. The percent hemolysis was calculated for each concentration of the test article disclosed herein with each donor's blood sample. The hemolysis data are presented below:

| Donor #1 - Male | | | | |
|---|---|---|---|---|
| Treatment | Concentration (μg/ml) | $OD_{540}$ without Blood | $OD_{540}$ with Blood | % Hemolysis |
| Saline | — | — | 0.004 | 0 |
| Water | — | — | 0.934 | 100 |
| Test Article | 0.5 | −0.002 | 0.003 | 0.11 |
| Test Article | 2 | −0.001 | 0.005 | 0.22 |
| Test Article | 10 | −0.002 | 0.003 | 0.11 |
| Test Article | 20 | −0.002 | 0.005 | 0.32 |

| Donor #2 - Female | | | | |
|---|---|---|---|---|
| Treatment | Concentration (μg/ml) | $OD_{540}$ without Blood | $OD_{540}$ with Blood | % Hemolysis |
| Saline | — | — | 0.007 | 0 |
| Water | — | — | 0.965 | 100 |
| Test Article | 0.5 | −0.002 | 0.004 | −0.10 |
| Test Article | 2 | −0.001 | 0.003 | −0.31 |
| Test Article | 10 | −0.002 | 0.004 | −0.10 |
| Test Article | 20 | −0.002 | 0.005 | 0 |

| Donor #3 - Female | | | | |
|---|---|---|---|---|
| Treatment | Concentration (μg/ml) | $OD_{540}$ without Blood | $OD_{540}$ with Blood | % Hemolysis |
| Saline | — | — | 0.002 | 0 |
| Water | — | — | 0.802 | 100 |
| Test Article | 0.5 | −0.002 | 0.005 | 0.63 |
| Test Article | 2 | −0.001 | 0.005 | 0.50 |
| Test Article | 10 | −0.002 | 0.004 | 0.50 |
| Test Article | 20 | −0.002 | 0.005 | 0.63 |

| Donor #4 - Male | | | | |
|---|---|---|---|---|
| Treatment | Concentration (μg/ml) | $OD_{540}$ without Blood | $OD_{540}$ with Blood | % Hemolysis |
| Saline | — | — | 0.004 | 0 |
| Water | — | — | 0.972 | 100 |
| Test Article | 0.5 | −0.002 | 0.012 | 1.03 |
| Test Article | 2 | −0.001 | 0.005 | 0.21 |
| Test Article | 10 | −0.002 | 0.006 | 0.41 |
| Test Article | 20 | −0.002 | 0.013 | 1.14 |

The % Hemolysis data demonstrated that the cetirizine injection disclosed herein is substantially free of hemolytic effect. The test conducted herein was conducted at the request of the FDA and satisfy their standards for showing a lack of hemolytic potential. Thus, unlike the parent hydroxyzine, which requires an FDA warning label with regard to hydrolysis, the formulations disclosed herein are substantially free of hemolytic effect.

Efficacy

In one aspect, a clinical endpoint bioequivalence study to compare the efficacy of a non-sedating antihistamine or second or third generation antihistamine injection to diphenhydramine injection is performed. In another embodiment, the efficacy of a non-sedating antihistamine or second or third generation antihistamine injection is compared to placebo.

Pruritus and erythema: The primary efficacy endpoints include the pruritus severity score and the erythema severity score (scored on a 0=absent, 1=mild, 2=moderate, to 3=severe scale, at 0.5 increments), and the reduction of the scores following treatment. For clinical trials, patients with "score 1-3" (mild to severe) will be recruited.

The primary efficacy end points are the difference between the treatment disclosed herein and the treatment of placebo in the mean change from the baseline of the average of the pruritus severity score and the erythema severity score. The study will be designed to give a 90% power to detect a 0.5 unit mean difference for the primary efficacy endpoint at a two-sided alpha-level of 0.05.

In addition, the duration of pruritus as an efficacy end point that can be measured. Duration of pruritus is categorized as follows: 3 if >6 hours/24 hr, 2 if 1 to 6 hours/24 hr, 1 if less than 1 hour/24 hr, and 0 if no pruritus. The study will be designed to give a 90% power to detect a 0.5 unit mean reduction for the primary efficacy endpoint at a two-sided alpha-level of 0.05.

Angioedema: The primary efficacy endpoints for angioedema include the angioedema severity score (scored on a 0=absent, 1=mild, 2=moderate, to 3=severe scale, at 0.5 increments), and the reduction of the score following treatment.

Wheezing: The primary efficacy endpoints include the wheezing severity score (scored on a 0=absent, 1=mild, 2=moderate, to 3=severe scale, at 0.5 increments), and the reduction of the score following treatment.

Exemplary clinical studies include a randomized, double-blind, active and placebo—controlled trial of about 300 patients over the age of 12 with acute allergic syndromes. About 100 patients will be randomly assigned to each of the 3 treatments including a nonsedating antihistamine injection as disclosed herein, a diphenhydramine injection, or a placebo injection, all via intravenous, intramuscular or subcutaneous administration. Patients will be recruited at multiple centers, from emergency departments at urban hospitals and allergy clinics throughout the country. The primary endpoints will be the reduction of pruritus severity score, pruritus duration, erythema, angioedema, wheezing, number of urticaria areas, and/or number of erythema areas, at 2-4 hours after protocol treatment. Symptom scores will be also assessed at baseline.

A broad definition of allergic syndromes to approximate real-life emergency department (ED) approaches will be used to assess the patients with various symptoms and signs. Patients over the age of 12 will be considered for recruitment from the ED if they have the following syndromes after an ingested food or ingested, inhaled, or injected drug, after in contact with latex or bee stings: acute urticaria (score 1 and above), acute angioedema (score 1 and above), wheezing (score 1 and above), and acute pruritic rash (score 1 and above). These manifestations should have been present for no greater than 12 hours from the time of alleged allergen exposure. Pregnant patients will be excluded. Recruited patients will be randomly assigned to treatment with either 10 mg of cetirizine injection (the test product group, i.e. product of present disclosure), diphenhydramine 50 mg injection (the comparator or active control group) or placebo injection (placebo control group)

Each treatment designation will be blinded based on the randomization code. The physician who is unaware of the treatment content will administer the contents by means of intravenous (or intramuscular, or subcutaneous, depending on protocol requirement) injection to the subject. Supplemental medications, such as epinephrine, corticosteroids, bronchodilators, and additional doses of antihistamine may be administered at the discretion of the study physicians as a rescue procedure. Patients may also receive supplemental oxygen and intravenous fluids at the discretion of the study physicians as a rescue procedure. Patients will have heart rate, blood pressure, physical findings, side effects, and symptoms assessed at baseline, 1 hour, 2 hours and 4 hours relative to experimental treatment. Baseline temperatures will be also recorded. Clinical recording will include the presence and extent or severity scores of urticaria and erythema, angioedema, wheezing, pruritus, number of urticaria areas, number of erythema areas, abdominal distention or tenderness, and abdominal hyperactive bowel sounds. Historical features, physical findings (including heart rates, blood pressure, and respiratory rates), and treatments will be recorded on a study-specific data input form. The extent of involvement with urticaria and erythema will be assessed by using a check-off cartoon of body areas (similar to that used to assess burn area extent) printed on the data input sheet. Symptom scores will be assessed at baseline, 1 hour, and 2, or 4 hours by using a preprinted form with none (score 0), mild (score 1), moderate (score 2), and severe (score 3) check-off categories.

The primary variables of interest will be resolution or reduction of urticaria, angioedema, erythema, pruritus, wheezing, number of urticaria areas, and number of erythema areas. Changes in heart rates, respiratory rates, blood pressure, and symptoms will also be examined. The final disposition of the patient will be noted (admission, discharge, or leaving against medical advice). The study will be approved by the institutional review board, and informed written consent will be obtained from all patients.

Statistical assessment will be using bivariate $X_2$ analysis and analysis of variance or covariance (ANCOVA), multivariate logistic regression. Covariates will be included in some multivariate models. Analyses will be performed by using the SAS software. Certain statistical values are expressed with 90% confidence intervals (CIs).

The above clinical trials may be split into two separate studies. One study will be an active controlled study comparing the invention injectable product with diphenhydramine injection. The other will be a placebo controlled study comparing the invention injectable product with a placebo.

In addition, pediatric studies will be conducted on patients younger than the age of 12 with similar study design and lower drug dosage.

Prompt treatment with antihistamines is highly recommended to alleviate the symptoms of acute allergic reactions. Antihistamines are helpful in reducing histamine-mediated vasodilation and secondary edema. Commonly used drugs such as diphenhydramine injection provide $H_1$ blockade. Diphenhydramine reduces vasodilation in small blood vessels in the nose, eyes, and airways and provide some anticholinergic effects toward drying secretions. Diphenhydramine (1 to 2 mg/kg, up to a maximum of 50 mg, given IV or IM) is the drug of choice when treating acute allergic reactions. Concomitant administration of an $H_2$ agonist such as ranitidine (1 mg/kg IV) or cimetidine (4 mg/kg IV) is also of value to provide antihistaminic effect.

In one embodiment, the present disclosure includes injectable formulations of second and third generation antihistamines, or non-sedating antihistamines, via intravenous, intramuscular, or subcutaneous administration to provide an immediate onset of action. Such second and third generation antihistamines are commercially available as oral dosage forms as shown in the following table:

TABLE 2

| Second and third generation antihistamines | |
|---|---|
| | Currently marketed dosage form |
| Second generation antihistamines | |
| cetirizine | 10 mg tablet, once daily for adults over 6 |
| | 5 mg chewable, once daily for children under 6 |
| | AUC0-24 = about 4023 ng · hr/mL for adult dose of 10 mg; |
| | (range: about 2500 to about 5500 ng · hr/mL) |
| | AUC0-INF = about 4638 ng · hr/mL, for adult dose of 10 mg; |
| | (range: about 3000 to about 6200 ng · hr/mL) |
| loratidine | 10 mg tablet every 12 hours for adults over 6 |
| | 5 mg chewable every 12 hours for children 2-6 |
| | AUC0-24 = about 7.36 ng · hr/mL (fasting) |
| | AUC0-INF = about 7.90 ng · hr/mL (fasting) |
| | AUC0-24 = about 10.3 ng · hr/mL (fed) |
| | AUC0-INF = about 11.1 ng · hr/mL (fed) |
| Third generation antihistamines | |
| fexofenadine | 60 mg tablet twice daily or 180 mg tablet once daily for adults over 12 |

TABLE 2-continued

Second and third generation antihistamines

Currently marketed dosage form

| | |
|---|---|
| | 30 mg tablet once daily for children 6-11<br>AUC0-inf (60 mg) = about 958 ng · hr/mL<br>AUC0-inf (180 mg) = about 3397 ng · hr/mL<br>AUC0-INF (240 mg) = about 6571 ng · hr/mL |
| levocetirizine | 5 mg tablet, once daily for adults over 12<br>2.5 mg tablet once daily for children 6-11<br>1.25 mg (½ teaspoon oral solution) once daily for children 6 months to 5 years<br>AUC0-24 = about 3469 ng · hr/mL; (range: about 1500 to about 5000 ng · hr/mL)<br>AUC0-INF = about 3998 ng · hr/mL; (range: about 2000 to about 5500 ng · hr/mL) |
| desloratadine | 5 mg tablet once daily for adults over 12<br>1 teaspoonful (2.5 mg in 5 mL) once daily for children 6 to 11<br>½ teaspoonful (1.25 mg in 2.5 mL) once daily for children 12 months to 5 years<br>AUCSS = about 56.9 ng·hr/mL<br>AUC0-24 (single dose) = about 34.2 ng · hr/mL<br>AUC(single dose)0-inf = about 35.6 ng/hr/mL |

Particularly, the cetirizine based injectable described herein are believed to be particularly useful.

Additional non-sedating antihistamines include des-diphenhydramine, epinastine, azelastine, Acrivastine, Ebastine, carbastine, levocarbastine, Mizolastine, and Rupatadine.

Parenteral injectable formulations may be in unit dose form in ampoules, small volume parenteral (SVP) vials, large volume parenterals (SVP), pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, buffering, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

Parenteral injectable formulations are typically aqueous solutions which may contain excipients such as salts, carbohydrates and buffering agents (preferably at a pH of from 3 to 9.5), but, for some applications, they may be more suitably formulated as a sterile nonaqueous solution or as a dried form to be used in conjunction with a suitable vehicle such as sterile, pyrogen-free water.

In one embodiment, the injectable compositions contain a solution of one or more non-sedating antihistamines in an aqueous solvent combined with a buffer or pH adjusting agents having a pH of 3 to 9. The composition optionally contains at least one isotonicity agent. A water-insoluble inert gas may be carefully bubbled through the aqueous solvent to remove oxygen from the medium. Optionally the compositions contain at least one preservative and/or at least one solubility enhancing agent and/or at least one stabilizing agent. In some embodiments, the compositions are substantially free of preservatives.

In one embodiment, the non-sedating H1 antihistamine is cetirizine or a salt thereof. In another embodiment, the quantity of cetirizine or salt thereof in the injection formulation is 1-100 mg per milliliter of liquid, preferably 1.5-50 mg, more preferably 2-25 mg per milliliter of liquid. In some embodiments, the composition is 10 mg cetirizine per milliliter of liquid.

In another embodiment, the non-sedating H1 antihistamines is fexofenadine or a salt thereof. In yet another embodiment, the quantity of fexofenadine or salt thereof in the injection formulation is 1-200 mg per milliliter of liquid, preferably 1.5-180 mg, preferably 2-90 mg, more preferably 2.5-70 mg per milliliter of liquid.

In another embodiment, the injectable composition optionally comprises at least one H2 antihistamine, specifically ranitidine and cimetidine, more specifically ranitidine. Concomitant administration of an H2 agonist such as ranitidine (1 mg/kg IV) or cimetidine (4 mg/kg IV) may be of value to provide antihistaminic effect.

In one embodiment, disclosed herein is an injectable second or third generation antihistamine (non-sedating antihistamine) formulation, such as cetirizine. Also disclosed are methods of treating an acute allergic reaction comprising administering to an individual in need thereof an effective amount of an injectable composition comprising a second or third generation antihistamine (or non-sedating antihistamine). In specific embodiments, the antihistamine is not diphenhydramine. In other embodiments, the non-sedating antihistamine is selected from cetirizine, loratadine, levocetirizine, desloratadine, and fexofenadine, des-diphenhydramine, epinastine, azelastine, Acrivastine, Ebastine, carbastine, levocarbastine, Mizolastine, and Rupataline. Particularly, the non-sedating antihistamine is cetirizine.

In one embodiment, the injectable formulation further comprises at least one H2 receptor antagonist, such as ranitidine or cimetidine. In another embodiment, the injectable formulation further comprises epinephrine. In yet another embodiment, the injectable formulation further comprises at least one steroid, such as methylprednisolone or prednisolone.

In one embodiment, disclosed herein are methods of treating an acute allergic reaction comprising administering to an individual in need thereof an effective amount of an injectable composition comprising a second or third generation antihistamine (or non-sedating antihistamine), wherein the injectable composition is bioequivalent to an oral formulation of the $2_{nd}$ or $3_{rd}$ generation antihistamine.

| Non-sedating Antihistamine | Oral product | Dosage range of injectable formulation |
|---|---|---|
| Cetirizine | 10 mg tablet<br>10 mg chewable tablet<br>10 mg capsule<br>5 mg tablet<br>5 mg/5 mL syrup | about 2 mg to about 10 mg |
| Loratadine | 10 mg tablet<br>10 mg capsule<br>5 mg tablet<br>5 mg chewable tablet<br>0.5 mg/mL syrup<br>1 mg/mL suspension<br>1 mg/mL syrup | about 1 mg to about 10 mg |
| Fexofenadine | 180 mg tablet/capsule<br>60 mg tablet<br>30 mg tablet<br>30 mg/5 mL suspension | about 5 mg to about 180 mg |
| Levocetirizine | 5 mg tablet<br>2.5 mg tablet<br>2.5 mg/5 mL syrup | about 1 mg to about 5 mg |
| Desloratadine | 5 mg tablet<br>2.5 mg/5 mL syrup | about 1 mg to about 5 mg |

As used herein, the term equivalent to an oral product means that the 90% confidence limits of a ratio of a logarithmic transformed geometric mean of $AUC_{0-INF}$ and/or $AUC_{0-t}$ for the injectable formulation to a logarithmic transformed geometric mean of $AUC_{0-INF}$ and/or $AUC_{0-t}$ for the reference oral product are about 0.80 to about 1.25, specifically 0.80 to 1.25. "AUC" is the area under the curve of a graph of the measured concentration of an active agent (typically plasma concentration) vs. time, measured from one time point to another time point. For example $AUC_{0-t}$ is the area under the curve of plasma concentration versus time from time 0 to time t, the last blood draw time point. The $AUC_{0-\square}$ or $AUC_{0-INF}$ is the calculated area under the curve of plasma concentration versus time from time 0 to time infinity by extrapolation. In one embodiment, the $AUC_{0-INF}$ and/or $AUC_{0-t}$ are given in Table 2. In another embodiment, the $-AUC_{INF}$ and/or $AUC_{0-t}$ for the injectable formulation and the reference oral dosage form are given determined in a reference-controlled study.

In one embodiment, disclosed herein are methods of treating an acute allergic reaction including anaphylaxis comprising administering to an individual in need thereof an effective amount of an injectable composition comprising a second or third generation antihistamine (or non-sedating antihistamine), wherein the injectable composition is therapeutically equivalent to a reference diphenydramine injectable formulation. In one embodiment, the reference diphenydramine injectable formulation is a 50 mg/mL solution, and the dose is about 12.5-150 mg dose. Diphenhydramine injection is commercially available from Pfizer as Benadryl® Injection. Many generic versions of diphenhydramine injections are also available on the market. Therapeutic equivalence can be determined in a reference-controlled study using a diphenydramine injectable formulation as the reference.

The term "Therapeutic equivalence" can also be expressed as "clinical equivalence", "clinically bioequivalent", or "clinical endpoint bioequivalence". The term "equivalent" can also be expressed as "bioequivalent".

As used herein, therapeutically equivalent to a reference diphenydramine injectable formulation means that the test formulation has a 90% confidence interval around the difference in the reduction of at least one symptom of an acute allergic reaction including anaphylaxis of the test drug to the reference drug, for the per protocol evaluable population, within about −30.00 to about +30.00. In specific embodiments, the symptoms of anaphylaxis or an acute allergic reaction are, pruritus severity, pruritus duration, erythema, angioedema and/or wheezing reduction, and urticaria areas or erythema areas.

Predicted Results for Clinical Equivalence are Presented in Table 3:

| Treatment | N | Baseline | On Treatment adjusted mean | Difference from Placebo | 90% CI (−30.00, +30.00) |
|---|---|---|---|---|---|
| Pruritus severity score reduction ||||||
| Cetirizine 10 mg injection | About 100 | About 2.80 | About 1.70 | +0.05 | About (−3.00, 8.00) |
| Diphenhydramine 50 mg injection | About 100 | About 2.75 | About 1.65 | | |
| Pruritus duration reduction ||||||
| Cetirizine 10 mg injection | About 100 | | About 1.00 hr | −0.50 hr | About (−8.50, 3.50) |
| Diphenhydramine 50 mg injection | About 100 | | About 1.50 hr | | |
| Erythema Reduction ||||||
| Cetirizine 10 mg injection | About 100 | About 2.50 | About 1.0 | 0.00 | About (−10.00, 10.00) |
| Diphenhydramine 50 mg injection | About 100 | About 2.55 | About 1.0 | | |
| Angioedema Reduction ||||||
| Cetirizine 10 mg injection | About 100 | About 2.50 | About 1.0 | −0.25 | About (−10.00, 8.00) |
| Diphenhydramine 50 mg injection | About 100 | About 2.45 | About 1.25 | | |

-continued

| Treatment | N | Baseline | On Treatment adjusted mean | Difference from Placebo | 90% CI (−30.00, +30.00) |
|---|---|---|---|---|---|
| Wheezing reduction | | | | | |
| Cetirizine 10 mg injection | About 100 | About 2.45 | About 1.40 | +0.40 | About (−0.20, 15.00) |
| Diphenhydramine 50 mg injection | About 100 | About 2.55 | About 1.00 | | |
| Number of urticaria areas | | | | | |
| Cetirizine 10 mg injection | About 100 | About 4.2 | About 1.0 | −0.20 | About (−10.00, 8.00) |
| Diphenhydramine 50 mg injection | About 100 | About 4.0 | About 1.20 | | |
| Number of erythema areas | | | | | |
| Cetirizine 10 mg injection | About 100 | About 7.0 | About 1.0 | −1.0 | About (−15.00, 10.00) |
| Diphenhydramine 50 mg injection | About 100 | About 7.2 | About 2.0 | | |

Expected Results for Effectiveness Comparing to Placebo are Presented in Table 4:

| Treatment | N | Baseline | On Treatment adjusted mean | Difference from Placebo | P-value |
|---|---|---|---|---|---|
| Pruritus severity score reduction | | | | | |
| Cetirizine 10 mg injection | About 100 | About 2.80 | About 1.80 | −0.70 | <0.05 |
| Placebo injection | About 100 | About 2.75 | About 2.50 | | |
| Pruritus duration reduction | | | | | |
| Cetirizine 10 mg injection | About 100 | | About 1.50 hr | −2.5 hr | <0.05 |
| Placebo injection | About 100 | | About 4.00 hr | | |
| Erythema Reduction | | | | | |
| Cetirizine 10 mg injection | About 100 | About 2.50 | About 1.0 | −1.15 | <0.05 |
| Placebo injection | About 100 | About 2.55 | About 2.15 | | |
| Angioedema Reduction | | | | | |
| Cetirizine 10 mg injection | About 100 | About 2.50 | About 1.0 | −1.25 | <0.05 |
| Placebo injection | About 100 | About 2.45 | About 2.25 | | |
| Wheezing reduction | | | | | |
| Cetirizine 10 mg injection | About 100 | About 2.45 | About 1.40 | −0.75 | <0.05 |
| Placebo injection | About 100 | About 2.55 | About 2.15 | | |
| Number of urticaria areas | | | | | |
| Cetirizine 10 mg injection | About 100 | About 4.2 | About 1.0 | −2.8 | <0.05 |
| Placebo injection | About 100 | About 4.0 | About 3.8 | | |
| Number of erythema areas | | | | | |
| Cetirizine 10 mg injection | About 100 | About 6.0 | About 1.0 | −4.0 | <0.05 |
| Placebo injection | About 100 | About 6.2 | About 5.0 | | |

In one embodiment, disclosed herein are methods of treating an acute allergic reaction including anaphylaxis comprising administering to an individual in need thereof an effective amount of an injectable composition comprising a second or third generation antihistamine, the non-sedating antihistamine, wherein the injectable composition is therapeutically effective compared to placebo. As used herein, a placebo is an inactive pill, liquid, or powder that has no treatment value. In clinical trials, experimental treatments are often compared with placebos to assess the treatment's effectiveness. A placebo-controlled study is a method of investigation of drugs in which an inactive substance (the placebo) is given to one group of participants, while the drug being tested is given to another group. The results obtained in the two groups are then compared to see if the investigational treatment is more effective in treating the condition.

As used herein, therapeutically effective compared to placebo means that the treatment of this invention is statistically superior ($p<0.05$) to a placebo in the reduction of at least one symptom of anaphylaxis or an acute allergic reaction, wherein the symptom is pruritus severity, pruritus duration, erythema, angioedema, urticaria areas, erythema areas, and/or wheezing.

The methods described herein optionally further comprise administering a second active agent as well as the second or third generation antihistamine. In one embodiment, the second active agent is an H2 receptor antagonist, such as ranitidine or cimetidine. In another embodiment, the second active agent is epinephrine. In yet another embodiment, the second active agent comprises at least one steroid, such as methylprednisolone or prednisolone. In one embodiment, the methods disclosed herein further comprise administering a second active agent comprising ranitidine, cimetidine, epinephrine, methylprednisolone, prednisolone, or a combination thereof.

Embodiments of this invention are described herein, including the best mode known to the inventors for carrying out the invention. Variations of those preferred embodiments would become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for treating angioedema associated with an acute allergic reaction comprising:
administering to a patient in an emergency situation in need of such treatment an injection composition comprising racemic cetirizine or a pharmaceutically acceptable salt thereof, in an amount of effective to treat said angioedema associated with an acute allergic reaction, wherein the injection composition is an aqueous solution having a pH of 3 to 9, and wherein administering comprises administration of 1 to 20 mg of racemic cetirizine.

2. The method of claim 1, wherein said injection comprises:
about 0.1% to about 2% w/v of cetirizine or a pharmaceutically acceptable salt thereof;
about 0.1 to about 0.9% w/v NaCl;
with pH adjusted to about 3 to about 9; and Q.S. water.

3. The method of claim 1, wherein said injection is an intravenous injection comprising:
about 1% w/v cetirizine or a pharmaceutically acceptable salt thereof;
about 0.65% w/v NaCl; and
adjusted to about pH 5.4;
in a 1 mL single dosage form.

4. The method of claim 1, wherein administering the cetirizine injection while minimizes sedation, is free of hemolytic potential, and does not demonstrate an effect on the QTc interval.

5. The method of claim 1, wherein administering is intravenous.

6. The method of claim 1, wherein administering is intramuscular.

7. The method of claim 1, wherein the 90% confidence limits of a ratio of a logarithmic transformed geometric mean of $AUC_{0-INF}$ for the injectable composition to a logarithmic transformed geometric mean of $AUC_{0-INF}$ for a reference oral product of cetirizine are 0.80 to 1.25.

8. The method of claim 1, wherein the injectable composition of cetirizine has a 90% confidence interval around the difference in the reduction of at least one symptom of angioedema associated with an acute allergic reaction to a reference injectable formulation, for the per protocol evaluable population, within about −30.00 to about +30.00.

9. The method of claim 8, wherein the reference injectable formulation is a 12.5-150 mg dose of a 50 mg/mL diphenydramine injectable formulation.

10. The method of claim 1, wherein the injectable composition further comprises a second active agent comprising ranitidine, cimetidine, epinephrine, methylprednisolone, prednisolone, or a combination thereof.

11. The method of claim 1, wherein the patient is a human or animal patient.

12. The method of claim 1, wherein the acute allergic reaction is anaphylaxis.

* * * * *